United States Patent
Bertagnoli et al.

(10) Patent No.: US 9,254,139 B2
(45) Date of Patent: Feb. 9, 2016

(54) DRILLING/MILLING GUIDE AND KEEL CUT PREPARATION SYSTEM

(71) Applicant: DePuy Synthes Products, Inc., Raynham, MA (US)

(72) Inventors: Rudolf Bertagnoli, Vienna (AT); Daniel Murrey, Charlotte, NC (US); John P. Furda, Hamilton, NJ (US); Marc Reichen, West Chester, PA (US); David Gerber, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 371 days.

(21) Appl. No.: 13/679,486

(22) Filed: Nov. 16, 2012

(65) Prior Publication Data

US 2013/0079783 A1    Mar. 28, 2013

Related U.S. Application Data

(62) Division of application No. 12/375,710, filed as application No. PCT/US2007/074717 on Jul. 30, 2007, now Pat. No. 8,337,500.

(60) Provisional application No. 60/834,178, filed on Jul. 31, 2006.

(51) Int. Cl.
*A61B 17/16* (2006.01)
*A61B 17/17* (2006.01)
(Continued)

(52) U.S. Cl.
CPC .............. *A61B 17/17* (2013.01); *A61B 17/1671* (2013.01); *A61B 17/1757* (2013.01); *A61F 2/4425* (2013.01); *A61F 2/4611* (2013.01); *A61F 2/4684* (2013.01); *A61B 2017/1602* (2013.01); *A61F 2002/305* (2013.01); *A61F 2002/30383* (2013.01); *A61F 2002/30604* (2013.01); *A61F 2002/30662* (2013.01); *A61F 2002/30884* (2013.01); *A61F 2002/443* (2013.01); *A61F 2002/4628* (2013.01)

(58) Field of Classification Search
CPC ............ A61B 17/1671; A61B 17/1757; A61F 2/4611
See application file for complete search history.

(56) References Cited

U.S. PATENT DOCUMENTS

| 114,816 A | 5/1871 | Hiestand |
| 3,320,951 A | 5/1967 | Wittebol |

(Continued)

FOREIGN PATENT DOCUMENTS

| CH | 624 573 | 8/1981 |
| CN | 1805720 | 7/2006 |

(Continued)

OTHER PUBLICATIONS

Derwent abstract of cited reference to Gau, FR 2737656 Al, (2 pages), 1997.

(Continued)

*Primary Examiner* — David Bates
(74) *Attorney, Agent, or Firm* — Baker & Hostetler LLP

(57) ABSTRACT

An instrument system, associated milling or drilling guide and method include use of a trial implant of a size corresponding to an actual implant for the intervertebral space, with a milling guide mounted on the trial implant. The system also includes a cutting tool which is used to form a cutout in an adjacent vertebra.

26 Claims, 14 Drawing Sheets

(51) Int. Cl.
*A61F 2/44* (2006.01)
*A61F 2/46* (2006.01)
*A61F 2/30* (2006.01)

(56) References Cited

U.S. PATENT DOCUMENTS

| | | |
|---|---|---|
| 3,486,505 A | 12/1969 | Morrison |
| 3,510,883 A | 5/1970 | Cathcart |
| 3,579,829 A | 5/1971 | Sampson |
| 3,740,769 A | 6/1973 | Haboush |
| 3,875,595 A | 4/1975 | Froning |
| 3,903,549 A | 9/1975 | Deyerle |
| D243,286 S | 2/1977 | Deyerle |
| 4,021,864 A | 5/1977 | Waugh |
| 4,034,746 A | 7/1977 | Williams |
| 4,038,897 A | 8/1977 | Murray et al. |
| 4,038,987 A | 8/1977 | Komiya |
| 4,232,404 A | 11/1980 | Samuelson et al. |
| 4,309,777 A | 1/1982 | Patil |
| 4,349,921 A | 9/1982 | Kuntz |
| 4,466,429 A | 8/1984 | Loscher et al. |
| 4,467,802 A | 8/1984 | Maslanka |
| 4,470,158 A | 9/1984 | Pappas et al. |
| 4,545,374 A | 10/1985 | Jacobson |
| 4,550,450 A | 11/1985 | Kinnett |
| 4,622,959 A | 11/1986 | Marcus |
| 4,653,487 A | 3/1987 | Maale |
| 4,681,589 A | 7/1987 | Tronzo |
| 4,697,586 A | 10/1987 | Gazale |
| 4,714,469 A | 12/1987 | Kenna |
| 4,736,738 A | 4/1988 | Lipovsek et al. |
| 4,743,262 A | 5/1988 | Tronzo |
| 4,759,766 A | 7/1988 | Buettner-Janz et al. |
| 4,759,769 A | 7/1988 | Hedman et al. |
| 4,770,661 A | 9/1988 | Oh |
| 4,805,607 A | 2/1989 | Engelhardt et al. |
| 4,863,476 A | 9/1989 | Shepperd |
| 4,874,389 A | 10/1989 | Downey |
| 4,875,474 A | 10/1989 | Border |
| 4,878,915 A | 11/1989 | Brantigan |
| 4,892,545 A | 1/1990 | Day et al. |
| 4,898,161 A | 2/1990 | Grundei |
| 4,932,975 A | 6/1990 | Main et al. |
| 4,936,863 A | 6/1990 | Hofmann |
| 4,946,378 A | 8/1990 | Hirayama et al. |
| 4,997,432 A | 3/1991 | Keller |
| 5,002,576 A | 3/1991 | Fuhrmann et al. |
| 5,004,476 A | 4/1991 | Cook |
| 5,035,716 A | 7/1991 | Downey |
| 5,037,438 A | 8/1991 | Davidson |
| 5,062,850 A | 11/1991 | MacMillan et al. |
| 5,071,437 A | 12/1991 | Steffee |
| 5,108,442 A | 4/1992 | Smith |
| 5,122,130 A | 6/1992 | Keller |
| 5,171,280 A | 12/1992 | Baumgartner |
| 5,192,327 A | 3/1993 | Brantigan |
| 5,211,645 A | 5/1993 | Baumgart et al. |
| 5,228,455 A | 7/1993 | Barcel |
| 5,236,460 A | 8/1993 | Barber |
| 5,258,031 A | 11/1993 | Salib et al. |
| 5,271,737 A | 12/1993 | Baldwin et al. |
| 5,282,868 A | 2/1994 | Bahler |
| 5,290,312 A | 3/1994 | Kojimoto et al. |
| 5,306,308 A | 4/1994 | Gross et al. |
| 5,306,309 A | 4/1994 | Wagner et al. |
| 5,314,477 A | 5/1994 | Marnay |
| 5,326,366 A | 7/1994 | Pascarella et al. |
| 5,336,232 A | 8/1994 | Green et al. |
| 5,344,458 A | 9/1994 | Bonutti |
| 5,364,397 A | 11/1994 | Hayes et al. |
| 5,370,697 A | 12/1994 | Baumgartner |
| 5,383,888 A | 1/1995 | Zvenyatsky et al. |
| 5,395,317 A | 3/1995 | Kambin |
| 5,401,269 A | 3/1995 | Buttner-Janz et al. |
| 5,409,492 A | 4/1995 | Jones et al. |
| 5,423,825 A | 6/1995 | Levine |
| 5,425,773 A | 6/1995 | Boyd et al. |
| 5,431,658 A | 7/1995 | Moskovich |
| 5,443,514 A | 8/1995 | Steffee |
| 5,458,641 A | 10/1995 | Ramirez Jimenez |
| 5,484,437 A | 1/1996 | Michelson |
| 5,489,307 A | 2/1996 | Kuslich et al. |
| 5,501,654 A | 3/1996 | Failla et al. |
| 5,505,732 A | 4/1996 | Michelson |
| 5,507,816 A | 4/1996 | Bullivant |
| 5,509,934 A | 4/1996 | Cohen |
| 5,522,899 A | 6/1996 | Michelson |
| 5,534,029 A | 7/1996 | Shima |
| 5,534,030 A | 7/1996 | Navarro et al. |
| 5,554,191 A | 9/1996 | Lahille et al. |
| 5,556,431 A | 9/1996 | Buttner-Janz et al. |
| 5,562,736 A | 10/1996 | Ray et al. |
| 5,562,738 A | 10/1996 | Boyd et al. |
| 5,571,109 A | 11/1996 | Bertagnoli |
| 5,591,235 A | 1/1997 | Kuslich |
| 5,609,636 A | 3/1997 | Kohrs et al. |
| 5,658,347 A | 8/1997 | Sarkisian et al. |
| 5,676,701 A | 10/1997 | Yuan et al. |
| 5,683,465 A | 11/1997 | Shinn et al. |
| 5,702,469 A | 12/1997 | Whipple et al. |
| 5,702,486 A | 12/1997 | Craig et al. |
| 5,716,415 A | 2/1998 | Steffee |
| 5,720,751 A | 2/1998 | Jackson |
| 5,722,977 A | 3/1998 | Wilhelmy |
| 5,755,798 A | 5/1998 | Papavero et al. |
| 5,755,811 A | 5/1998 | Tanamal et al. |
| 5,776,199 A | 7/1998 | Michelson |
| 5,782,830 A | 7/1998 | Farris |
| 5,782,832 A | 7/1998 | Larsen et al. |
| 5,797,909 A | 8/1998 | Michelson |
| 5,800,547 A | 9/1998 | Schafer et al. |
| 5,824,094 A | 10/1998 | Serhan et al. |
| D401,335 S | 11/1998 | Koros et al. |
| 5,865,848 A | 2/1999 | Baker |
| 5,885,299 A | 3/1999 | Winslow et al. |
| 5,885,300 A | 3/1999 | Tokuhashi et al. |
| 5,888,226 A | 3/1999 | Rogozinski |
| 5,895,428 A | 4/1999 | Berry |
| 5,897,593 A | 4/1999 | Kohrs et al. |
| 5,899,901 A | 5/1999 | Middleton |
| 5,899,941 A | 5/1999 | Nishijima et al. |
| 5,951,564 A | 9/1999 | Schroder et al. |
| 6,006,174 A | 12/1999 | Lin et al. |
| 6,010,502 A | 1/2000 | Bagby |
| 6,017,342 A | 1/2000 | Rinner |
| 6,033,405 A | 3/2000 | Winslow et al. |
| 6,036,692 A | 3/2000 | Burel et al. |
| 6,042,582 A | 3/2000 | Ray et al. |
| 6,059,790 A | 5/2000 | Sand et al. |
| 6,063,088 A | 5/2000 | Winslow |
| 6,063,121 A | 5/2000 | Xavier et al. |
| 6,080,155 A | 6/2000 | Michelson |
| 6,083,225 A | 7/2000 | Winslow et al. |
| 6,083,228 A | 7/2000 | Michelson |
| 6,086,595 A | 7/2000 | Yonemura et al. |
| 6,096,038 A | 8/2000 | Michelson |
| 6,096,080 A | 8/2000 | Nicholson et al. |
| 6,102,950 A | 8/2000 | Vaccaro |
| 6,102,954 A | 8/2000 | Albrektsson et al. |
| 6,110,179 A | 8/2000 | Flivik et al. |
| 6,113,602 A | 9/2000 | Sand |
| 6,113,637 A | 9/2000 | Gill et al. |
| 6,113,638 A | 9/2000 | Williams et al. |
| 6,117,174 A | 9/2000 | Nolan |
| 6,126,660 A | 10/2000 | Dietz |
| 6,126,674 A | 10/2000 | Janzen |
| 6,146,421 A | 11/2000 | Gordon et al. |
| 6,156,040 A | 12/2000 | Yonemura et al. |
| 6,159,215 A | 12/2000 | Urbahns et al. |
| 6,171,339 B1 | 1/2001 | Houfburg et al. |
| 6,174,311 B1 | 1/2001 | Branch et al. |
| 6,224,599 B1 | 5/2001 | Baynham et al. |
| 6,238,414 B1 | 5/2001 | Griffiths |
| 6,241,769 B1 | 6/2001 | Nicholson et al. |

(56) References Cited

U.S. PATENT DOCUMENTS

| | | |
|---|---|---|
| 6,251,140 B1 | 6/2001 | Marino et al. |
| 6,261,296 B1 | 7/2001 | Aebi et al. |
| 6,264,655 B1 | 7/2001 | Pisharodi |
| 6,270,498 B1 | 8/2001 | Michelson |
| 6,296,647 B1 | 10/2001 | Robioneck et al. |
| 6,309,421 B1 | 10/2001 | Pisharodi |
| 6,368,350 B1 | 4/2002 | Erickson et al. |
| 6,368,351 B1 | 4/2002 | Glenn et al. |
| 6,368,353 B1 | 4/2002 | Arcand |
| 6,402,785 B1 | 6/2002 | Zdeblick et al. |
| 6,413,278 B1 | 7/2002 | Marchosky |
| 6,436,098 B1 | 8/2002 | Michelson |
| 6,436,139 B1 | 8/2002 | Shapiro et al. |
| 6,440,142 B1 | 8/2002 | Ralph et al. |
| 6,440,168 B1 | 8/2002 | Cauthen |
| 6,440,169 B1 | 8/2002 | Elberg et al. |
| 6,447,547 B1 | 9/2002 | Michelson |
| 6,478,800 B1 | 11/2002 | Fraser et al. |
| 6,478,801 B1 | 11/2002 | Ralph et al. |
| 6,478,823 B1 | 11/2002 | Michelson |
| 6,500,206 B1 | 12/2002 | Bryan |
| 6,517,544 B1 | 2/2003 | Michelson |
| 6,524,318 B1 | 2/2003 | Longhini et al. |
| 6,558,424 B2 | 5/2003 | Thalgott |
| 6,565,574 B2 | 5/2003 | Michelson |
| 6,595,995 B2 | 7/2003 | Zdeblick et al. |
| 6,599,294 B2 | 7/2003 | Fuss et al. |
| 6,610,065 B1 | 8/2003 | Branch et al. |
| 6,613,091 B1 | 9/2003 | Zdeblick et al. |
| 6,626,943 B2 | 9/2003 | Eberlein et al. |
| 6,635,060 B2 | 10/2003 | Hanson et al. |
| 6,641,582 B1 | 11/2003 | Hanson et al. |
| 6,641,614 B1 | 11/2003 | Wagner et al. |
| 6,652,533 B2 | 11/2003 | O'Neil |
| 6,652,534 B2 | 11/2003 | Zucherman et al. |
| 6,679,886 B2 | 1/2004 | Weikel et al. |
| 6,712,819 B2 | 3/2004 | Zucherman et al. |
| 6,712,825 B2 | 3/2004 | Aebi et al. |
| 6,733,505 B2 | 5/2004 | Li |
| 6,740,118 B2 | 5/2004 | Eisermann |
| 6,746,454 B2 | 6/2004 | Winterbottom et al. |
| 6,755,841 B2 | 6/2004 | Fraser et al. |
| 6,770,074 B2 | 8/2004 | Michelson |
| 6,824,565 B2 | 11/2004 | Muhanna et al. |
| 6,875,213 B2 | 4/2005 | Michelson |
| 6,896,676 B2 | 5/2005 | Zubok et al. |
| 6,936,071 B1 | 8/2005 | Marnay et al. |
| 6,964,687 B1 | 11/2005 | Bernard et al. |
| 6,966,912 B2 | 11/2005 | Michelson |
| 7,037,340 B2 | 5/2006 | Gau |
| 7,048,766 B2 | 5/2006 | Ferree |
| 7,081,120 B2 | 7/2006 | Li et al. |
| 7,083,649 B2 | 8/2006 | Zucherman et al. |
| 7,118,580 B1 | 10/2006 | Beyersdorff et al. |
| 7,169,182 B2 | 1/2007 | Errico et al. |
| 7,204,852 B2 | 4/2007 | Marnay et al. |
| 7,238,203 B2 | 7/2007 | Bagga et al. |
| 7,252,673 B2 | 8/2007 | Lim |
| 7,491,204 B2 | 2/2009 | Marnay |
| 7,547,309 B2 | 6/2009 | Bertagnoli et al. |
| 7,575,576 B2 | 8/2009 | Zubok et al. |
| 7,641,692 B2 | 1/2010 | Bryan et al. |
| 7,766,914 B2 | 8/2010 | McCormack et al. |
| 7,803,162 B2 | 9/2010 | Marnay et al. |
| 7,811,325 B2 | 10/2010 | Cannon et al. |
| 7,857,856 B2 | 12/2010 | Trieu |
| 8,025,684 B2 | 9/2011 | Garcia-Bengochea et al. |
| 8,092,542 B2 | 1/2012 | Bryan |
| 8,328,814 B2 * | 12/2012 | Klingseis et al. ............... 606/99 |
| 8,337,500 B2 | 12/2012 | Bertagnoli et al. |
| 2001/0010002 A1 | 7/2001 | Michelson |
| 2002/0016633 A1 | 2/2002 | Lin et al. |
| 2002/0049497 A1 | 4/2002 | Mason |
| 2002/0065558 A1 | 5/2002 | Varga et al. |
| 2002/0072752 A1 | 6/2002 | Zucherman et al. |
| 2002/0077702 A1 | 6/2002 | Castro |
| 2002/0091392 A1 | 7/2002 | Michelson |
| 2002/0099377 A1 | 7/2002 | Zucherman et al. |
| 2002/0111679 A1 | 8/2002 | Zucherman et al. |
| 2002/0120259 A1 | 8/2002 | Lettice et al. |
| 2002/0165612 A1 | 11/2002 | Gerber et al. |
| 2003/0028197 A1 | 2/2003 | Hanson et al. |
| 2003/0032962 A1 | 2/2003 | McGahan et al. |
| 2003/0045884 A1 | 3/2003 | Robie et al. |
| 2003/0055434 A1 | 3/2003 | O'Neil |
| 2003/0069586 A1 | 4/2003 | Errico et al. |
| 2003/0083747 A1 | 5/2003 | Winterbottom et al. |
| 2003/0135275 A1 | 7/2003 | Garcia et al. |
| 2003/0135277 A1 | 7/2003 | Bryan et al. |
| 2003/0171756 A1 | 9/2003 | Fallin et al. |
| 2003/0191534 A1 | 10/2003 | Viart et al. |
| 2003/0195631 A1 | 10/2003 | Ferree |
| 2003/0208273 A1 | 11/2003 | Eisermann et al. |
| 2003/0233097 A1 | 12/2003 | Ferree |
| 2003/0233145 A1 | 12/2003 | Landry et al. |
| 2004/0002758 A1 | 1/2004 | Landry et al. |
| 2004/0002761 A1 | 1/2004 | Rogers et al. |
| 2004/0010316 A1 | 1/2004 | William et al. |
| 2004/0024462 A1 | 2/2004 | Ferree et al. |
| 2004/0030387 A1 | 2/2004 | Landry et al. |
| 2004/0097929 A1 | 5/2004 | Branch et al. |
| 2004/0117022 A1 | 6/2004 | Marnay et al. |
| 2004/0133278 A1 | 7/2004 | Marino et al. |
| 2004/0143332 A1 | 7/2004 | Krueger et al. |
| 2004/0162563 A1 | 8/2004 | Michelson |
| 2004/0172133 A1 | 9/2004 | Gerber et al. |
| 2004/0176777 A1 | 9/2004 | Zubok et al. |
| 2004/0215198 A1 | 10/2004 | Marnay et al. |
| 2004/0225295 A1 | 11/2004 | Zubok et al. |
| 2004/0225366 A1 | 11/2004 | Eisermann et al. |
| 2005/0021042 A1 | 1/2005 | Marnay et al. |
| 2005/0021145 A1 | 1/2005 | de Villiers et al. |
| 2005/0021146 A1 | 1/2005 | de Villiers et al. |
| 2005/0043740 A1 | 2/2005 | Haid, Jr. et al. |
| 2005/0043802 A1 | 2/2005 | Eisermann et al. |
| 2005/0060035 A1 | 3/2005 | Errico et al. |
| 2005/0143747 A1 | 6/2005 | Zubok et al. |
| 2005/0143749 A1 | 6/2005 | Zalenski et al. |
| 2005/0159818 A1 | 7/2005 | Blain |
| 2005/0159819 A1 * | 7/2005 | McCormack et al. ..... 623/17.16 |
| 2005/0165408 A1 | 7/2005 | Puno et al. |
| 2005/0228500 A1 | 10/2005 | Kim et al. |
| 2005/0246022 A1 | 11/2005 | Zubok et al. |
| 2005/0251260 A1 | 11/2005 | Gerber et al. |
| 2005/0256578 A1 | 11/2005 | Blatt et al. |
| 2005/0261769 A1 | 11/2005 | Moskowitz et al. |
| 2005/0267581 A1 | 12/2005 | Marnay et al. |
| 2006/0030856 A1 | 2/2006 | Drewry et al. |
| 2006/0030860 A1 | 2/2006 | Peterman |
| 2006/0036326 A1 | 2/2006 | Baumgartner et al. |
| 2006/0041313 A1 | 2/2006 | Allard et al. |
| 2006/0064100 A1 | 3/2006 | Bertagnoli et al. |
| 2006/0089656 A1 | 4/2006 | Allard et al. |
| 2006/0100633 A1 | 5/2006 | Michelson |
| 2006/0116769 A1 | 6/2006 | Marnay et al. |
| 2006/0149273 A1 | 7/2006 | Ross et al. |
| 2006/0210594 A1 | 9/2006 | Trieu |
| 2006/0217809 A1 | 9/2006 | Albert et al. |
| 2006/0235533 A1 | 10/2006 | Blain |
| 2006/0241641 A1 | 10/2006 | Albans et al. |
| 2006/0265077 A1 | 11/2006 | Zwirkoski |
| 2007/0016221 A1 | 1/2007 | Beyersdorff et al. |
| 2007/0118145 A1 * | 5/2007 | Fischer et al. ............... 606/99 |
| 2007/0162134 A1 | 7/2007 | Marnay |
| 2007/0191857 A1 * | 8/2007 | Allard et al. ................ 606/90 |
| 2007/0198089 A1 | 8/2007 | Moskowitz et al. |
| 2007/0208345 A1 | 9/2007 | Marnay et al. |
| 2007/0208346 A1 | 9/2007 | Marnay et al. |
| 2007/0225812 A1 | 9/2007 | Gill |
| 2008/0140204 A1 | 6/2008 | Heinz |
| 2008/0228275 A1 | 9/2008 | Cannon et al. |
| 2009/0069894 A1 | 3/2009 | Duggal et al. |
| 2009/0076608 A1 | 3/2009 | Gordon et al. |
| 2010/0070042 A1 | 3/2010 | Bryan et al. |

(56) References Cited

U.S. PATENT DOCUMENTS

| | | |
|---|---|---|
| 2010/0217395 A1 | 8/2010 | Bertagnoli et al. |
| 2010/0324690 A1 | 12/2010 | Cannon et al. |
| 2011/0295374 A1 | 12/2011 | Bryan et al. |

FOREIGN PATENT DOCUMENTS

| | | |
|---|---|---|
| CN | 101027005 | 8/2007 |
| CN | 101631517 | 1/2010 |
| DE | 2263842 A1 | 7/1974 |
| DE | 2804936 A1 | 8/1979 |
| DE | 3023353 | 4/1981 |
| DE | 3526742 A1 | 1/1987 |
| DE | 4328690 B4 | 3/1995 |
| DE | 29916078 U1 | 11/1999 |
| DE | 202005018655 U1 | 1/2006 |
| DE | 102005056818 A1 * | 5/2007 |
| EP | 0077159 A1 | 4/1983 |
| EP | 0471821 B1 | 2/1992 |
| EP | 0333990 B1 | 7/1993 |
| EP | 0770367 | 5/1997 |
| EP | 0712607 B1 | 2/2002 |
| EP | 1793749 | 6/2007 |
| EP | 2120799 | 11/2009 |
| FR | 2718635 A1 | 10/1995 |
| FR | 2724108 | 3/1996 |
| FR | 2737656 A1 | 2/1997 |
| FR | 2742653 | 6/1997 |
| FR | 2795945 A1 | 1/2001 |
| JP | 2-261446 A | 10/1990 |
| JP | 2010-521244 | 6/2010 |
| WO | WO 91/13598 A1 | 9/1991 |
| WO | WO 98/34552 A1 | 8/1998 |
| WO | WO 01/01893 | 1/2001 |
| WO | WO 01/19295 A1 | 3/2001 |
| WO | WO 02/071986 A2 | 9/2002 |
| WO | WO 03/053290 A1 | 7/2003 |
| WO | WO 2004/019828 | 3/2004 |
| WO | WO 2004/098380 | 11/2004 |
| WO | WO 2005/051243 | 6/2005 |
| WO | WO 2005/053580 | 6/2005 |
| WO | WO 2005/055835 | 6/2005 |
| WO | WO 2005/099593 | 10/2005 |
| WO | WO 2006/012608 | 2/2006 |
| WO | WO 2006/033067 | 3/2006 |
| WO | WO 2006/036580 | 4/2006 |
| WO | WO2008/042155 A2 * | 9/2007 |
| WO | WO 2008/016872 | 2/2008 |
| WO | WO 2008/112956 | 9/2008 |
| ZA | 2009/05900 | 5/2010 |

OTHER PUBLICATIONS

European Patent Application No. EP 05795413: European Search Report dated Aug. 10, 2011, 7 pages.
In the United States Patent and Trademark Office, in Re. U.S. Appl. No. 10/070,823, Advisory Action dated Jun. 22, 2006.
In the United States Patent and Trademark Office, in Re. U.S. Appl. No. 10/070,823, Notice of Allowance dated Jul. 24, 2006.
In the United States Patent and Trademark Office, in Re. U.S. Appl. No. 10/318,078, Issue Notice dated Mar. 28, 2007.
In the United States Patent and Trademark Office, in Re. U.S. Appl. No. 10/318,078, Advisory Action dated Dec. 29, 2006.
In the United States Patent and Trademark Office, in Re. U.S. Appl. No. 10/318,078, Advisory Action dated Mar. 28, 2005.
In the United States Patent and Trademark Office, in Re. U.S. Appl. No. 10/947,660, filed Sep. 23, 2004: Non-Final Office Action dated Dec. 11, 2006.
In the United States Patent and Trademark Office, in Re. U.S. Appl. No. 10/947,660, filed Sep. 23, 2004: Non-Final Office Action dated Dec. 26, 2007.
In the United States Patent and Trademark Office, in Re. U.S. Appl. No. 10/947,660, filed Sep. 23, 2004: Non-Final Office Action dated Jul. 2, 2007.
In the United States Patent and Trademark Office, in Re. U.S. Appl. No. 10/947,660, filed Sep. 23, 2004: Non-Final Office Action dated Jul. 24, 2008.
In the United States Patent and Trademark Office, in Re. U.S. Appl. No. 10/947,660, filed Sep. 23, 2004: Notice of Allowance dated Feb. 9, 2009.
In the United States Patent and Trademark Office, in Re. U.S. Appl. No. 10/947,660, filed Sep. 23, 2004: Notice of Allowance dated Mar. 9, 2009.
In the United States Patent and Trademark Office, in Re. U.S. Appl. No. 10/947,660, filed Sep. 23, 2004: Notice of Issue dated May 27, 2009.
International Patent Application No. PCT/US2005/33007: International Search Report dated Oct. 20, 2006, 1 page.
International Patent Application No. PCT/US2008/056960: International Search Report dated Jul. 28, 2008, 6 pages.
In the United States Patent and Trademark Office, in Re. U.S. Appl. No. 10/070,823, Examiner Interview Summary Record and Notice of Allowance dated Jul. 13, 2006.
In the United States Patent and Trademark Office, in Re. U.S. Appl. No. 10/070,823, Final Rejection dated Aug. 23, 2005.
In the United States Patent and Trademark Office, in Re. U.S. Appl. No. 10/070,823, Non-Final Office Action dated Sep. 23, 2004.
In the United States Patent and Trademark Office, in Re. U.S. Appl. No. 10/318,078, Final Rejection dated Aug. 1, 2006.
In the United States Patent and Trademark Office, in Re. U.S. Appl. No. 10/318,078, Final Rejection dated Nov. 12, 2004.
In the United States Patent and Trademark Office, in Re. U.S. Appl. No. 10/318,078, Non-Final Office Action dated Apr. 21, 2004.
In the United States Patent and Trademark Office, in Re. U.S. Appl. No. 10/318,078, Non-Final Office Action dated Aug. 8, 2005.
In the United States Patent and Trademark Office, in Re. U.S. Appl. No. 10/318,078, Notice of Allowance dated Feb. 26, 2007.
In the United States Patent and Trademark Office, in Re. U.S. Appl. No. 10/622,535, filed Jul. 21, 2003: Non Final Office Action dated Apr. 26, 2007.
In the United States Patent and Trademark Office, in Re. U.S. Appl. No. 10/622,535, filed Jul. 21, 2003: Non Final Office Action dated Aug. 30, 2005.
In the United States Patent and Trademark Office, in Re. U.S. Appl. No. 10/622,535, filed Jul. 21, 2003: Final Rejection dated Feb. 6, 2009.
In the United States Patent and Trademark Office, in Re. U.S. Appl. No. 10/622,535, filed Jul. 21, 2003: Non Final Office Action dated Jan. 31, 2008.
In the United States Patent and Trademark Office, in Re. U.S. Appl. No. 10/622,535, filed Jul. 21, 2003: Non Final Office Action dated Nov. 8, 2006.
In the United States Patent and Trademark Office, in Re. U.S. Appl. No. 10/622,535, filed Jul. 21, 2003: Non Final Office Action dated Sep. 12, 2007.
In the United States Patent and Trademark Office, in Re. U.S. Appl. No. 10/622,535, filed Jul. 21, 2003: Notice of Allowance dated Jul. 20, 2009.
In the United States Patent and Trademark Office, in Re. U.S. Appl. No. 10/622,535, filed Jul. 21, 2003: Final Rejection dated May 23, 2006.
In the United States Patent and Trademark Office, in Re. U.S. Appl. No. 10/622,535, filed Jul. 21, 2003: Notice of Allowance dated Nov. 17, 2009.
In the United States Patent and Trademark Office, in Re. U.S. Appl. No. 11/512,327, filed Aug. 30, 2006, Notice of Allowance dated Oct. 8, 2009.
In the United States Patent and Trademark Office, in Re. U.S. Appl. No. 11/512,327, filed Aug. 30, 2006, Final Rejection dated Jun. 23, 2009.
In the United States Patent and Trademark Office, in Re. U.S. Appl. No. 11/512,327, filed Aug. 30, 2006, Non Final Rejection dated Oct. 6, 2008.

* cited by examiner

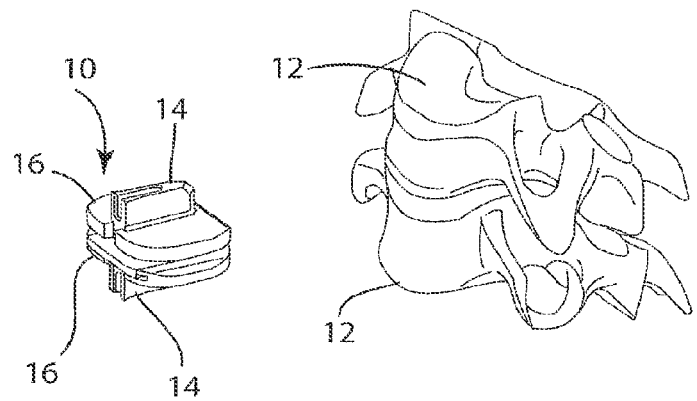
Fig. 1
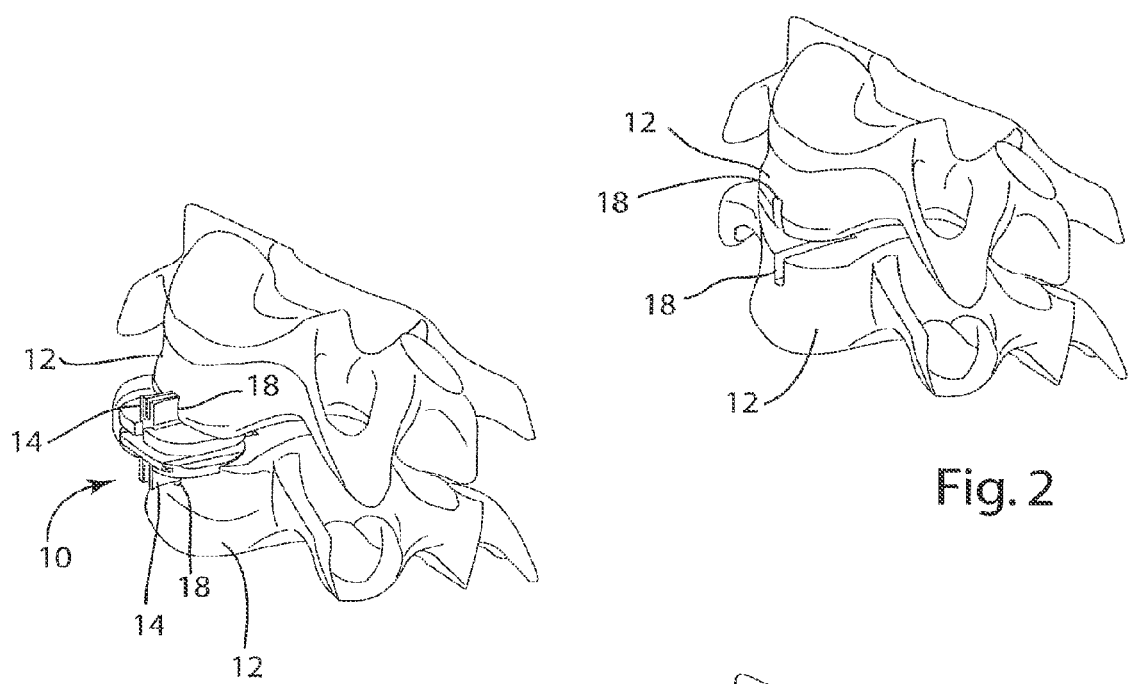
Fig. 2
Fig. 3
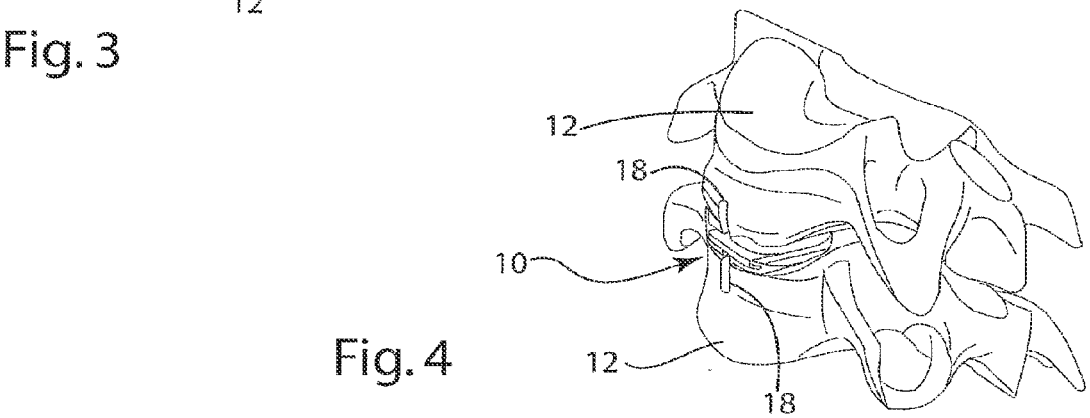
Fig. 4

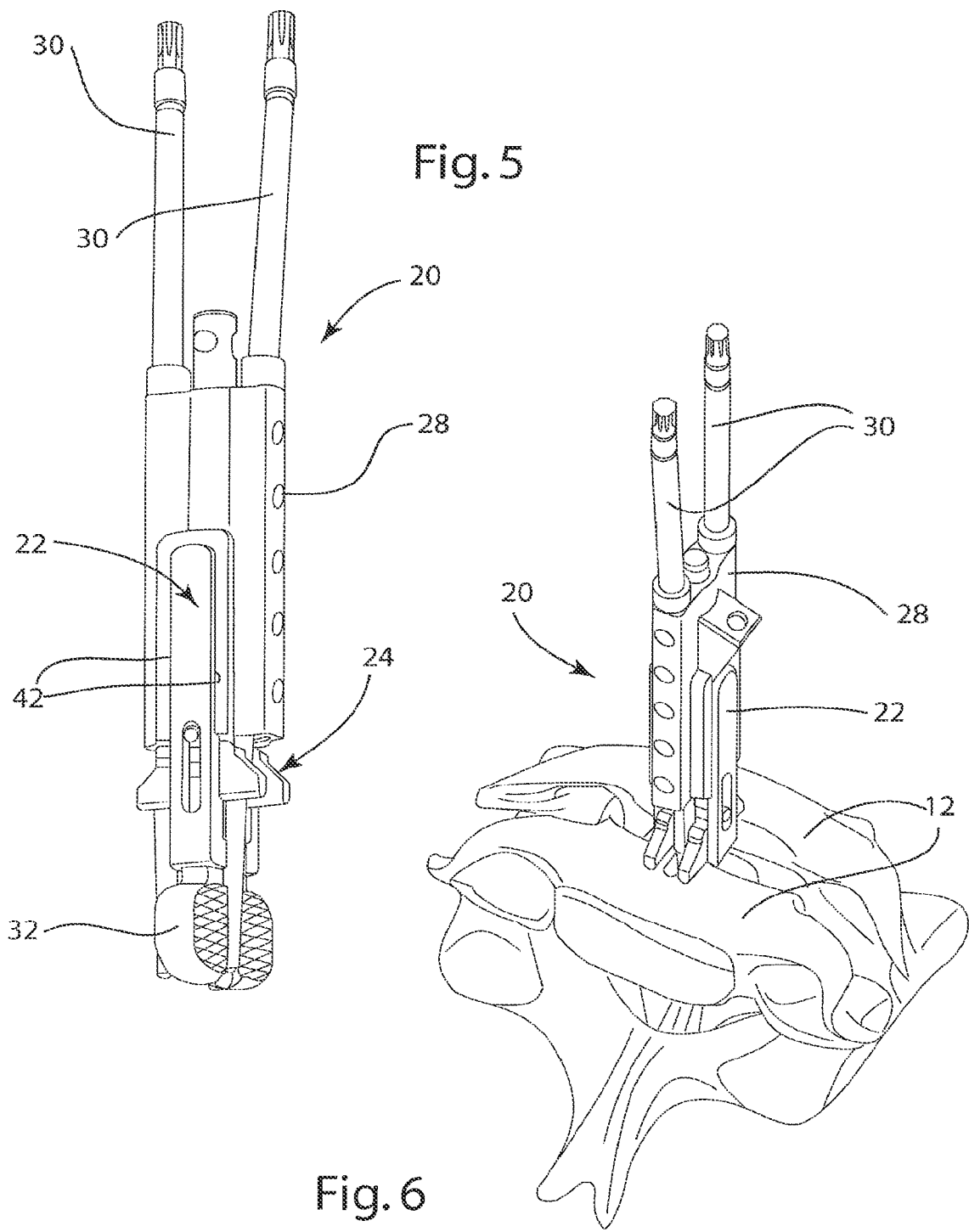

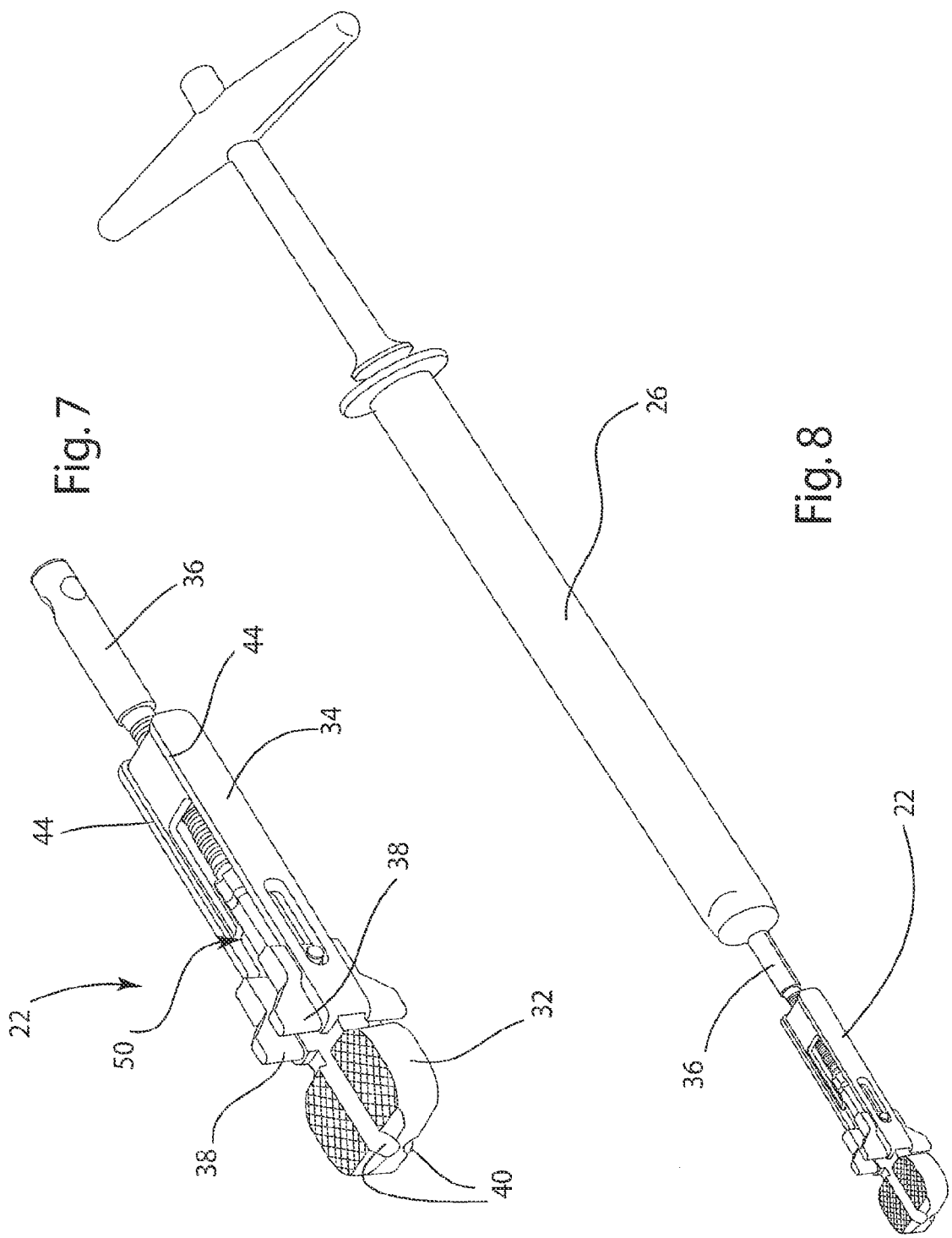

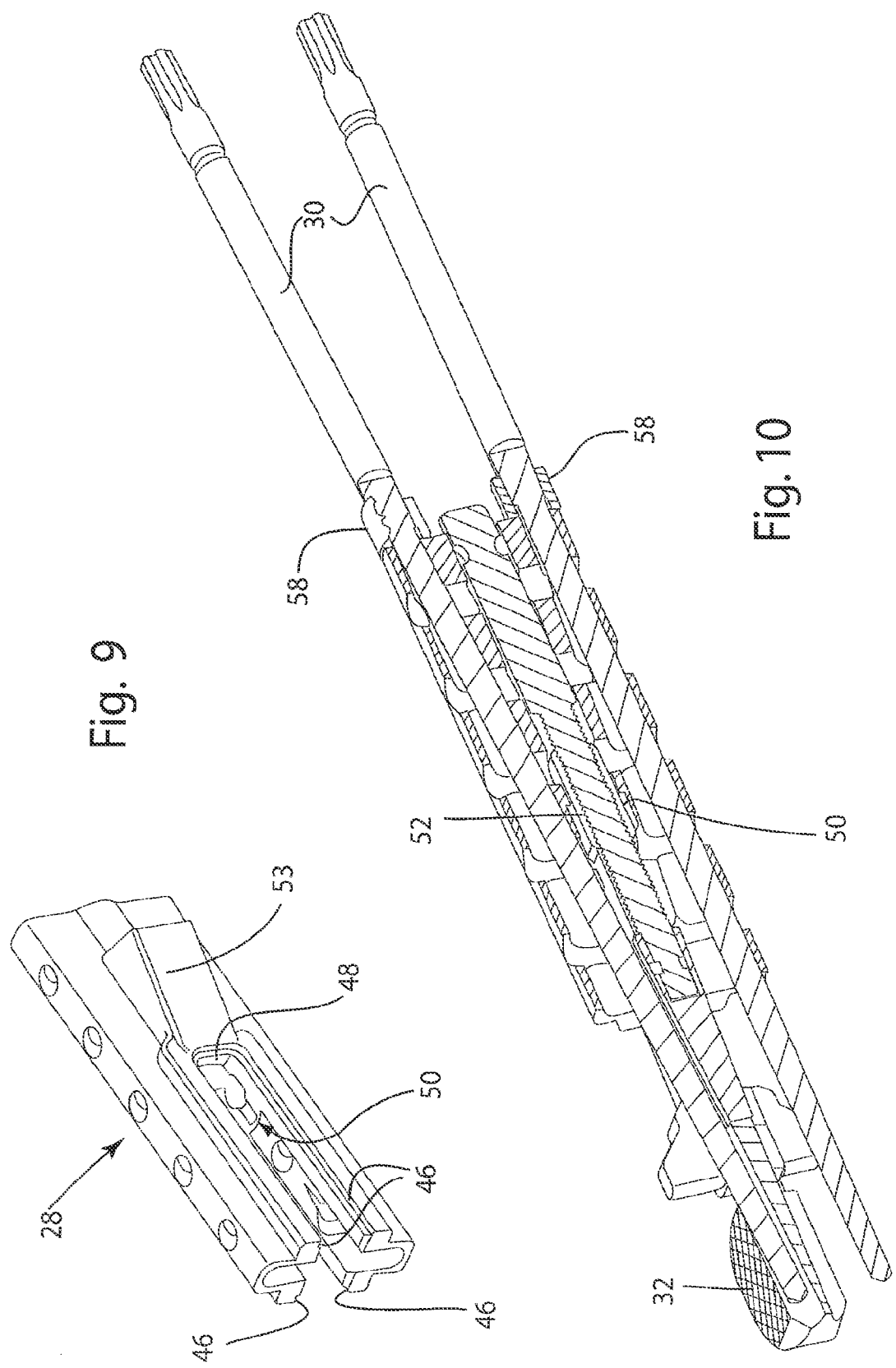

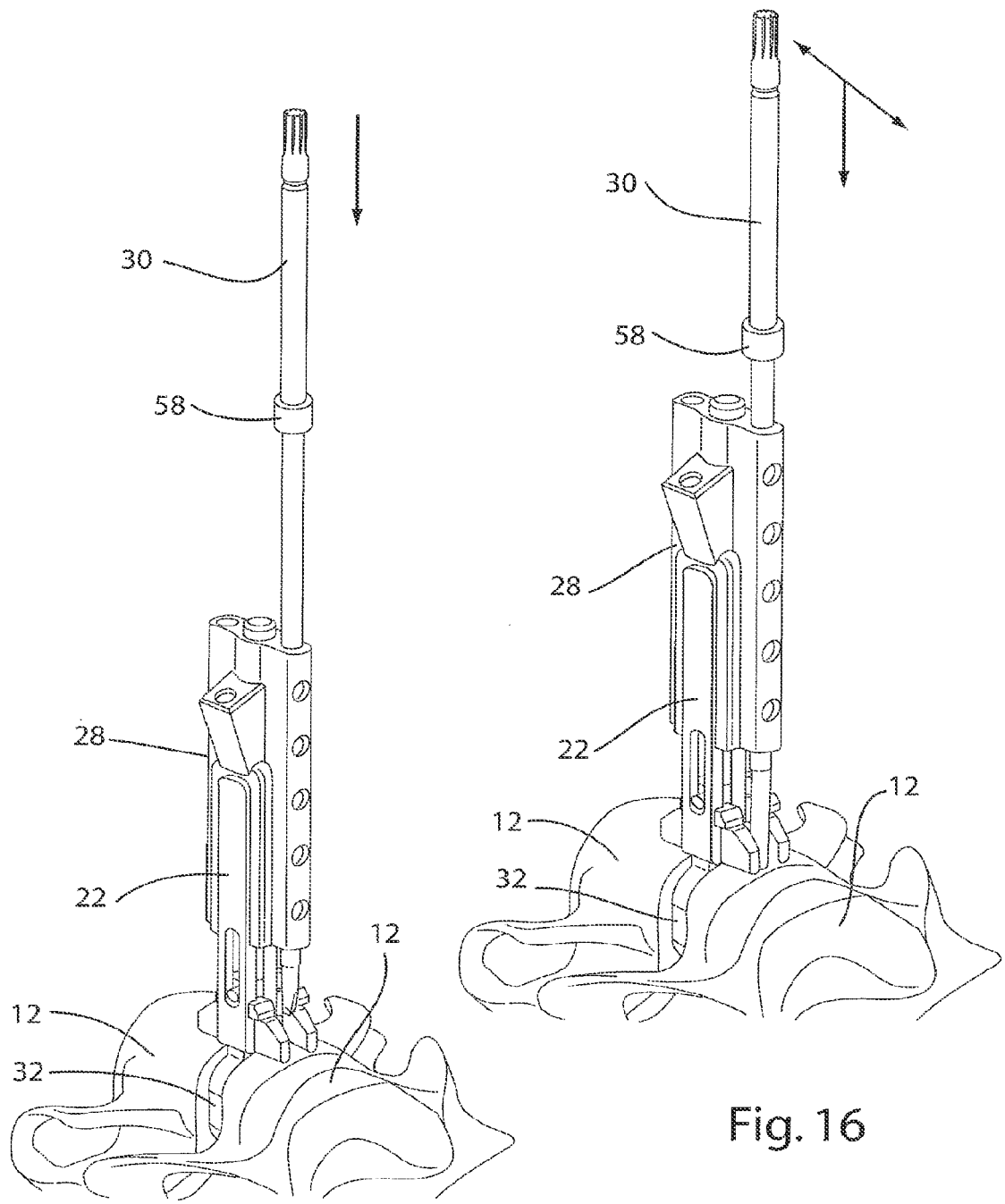

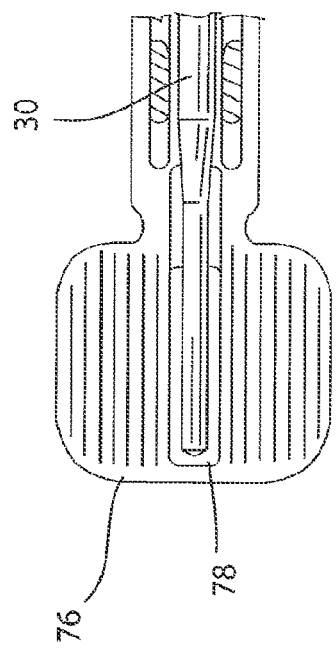
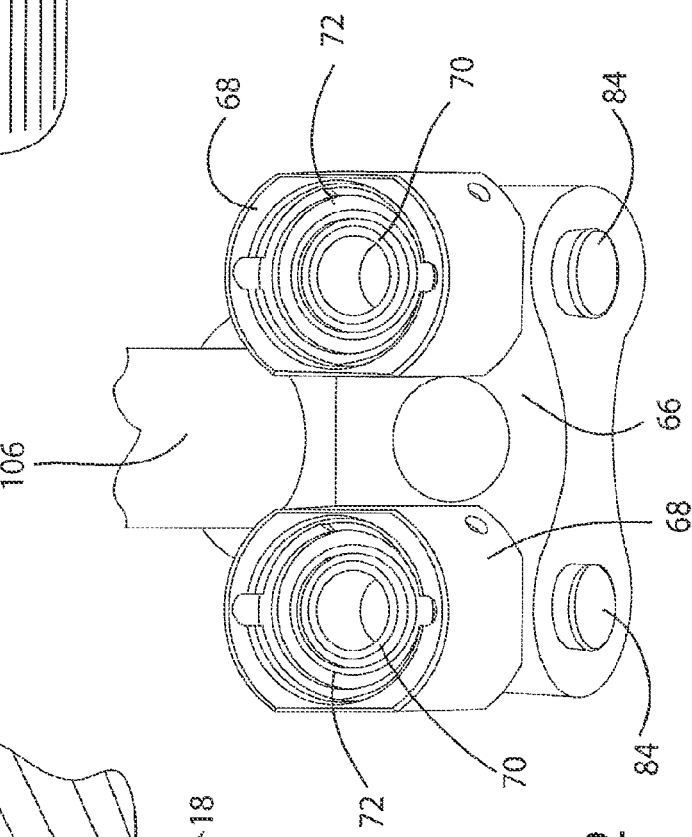
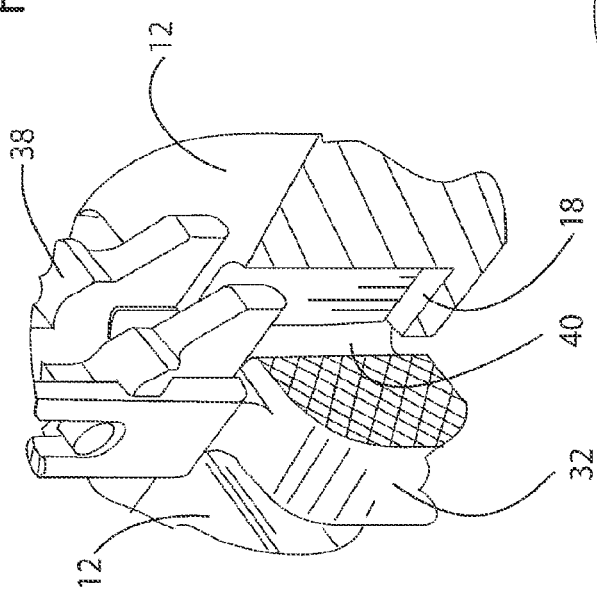

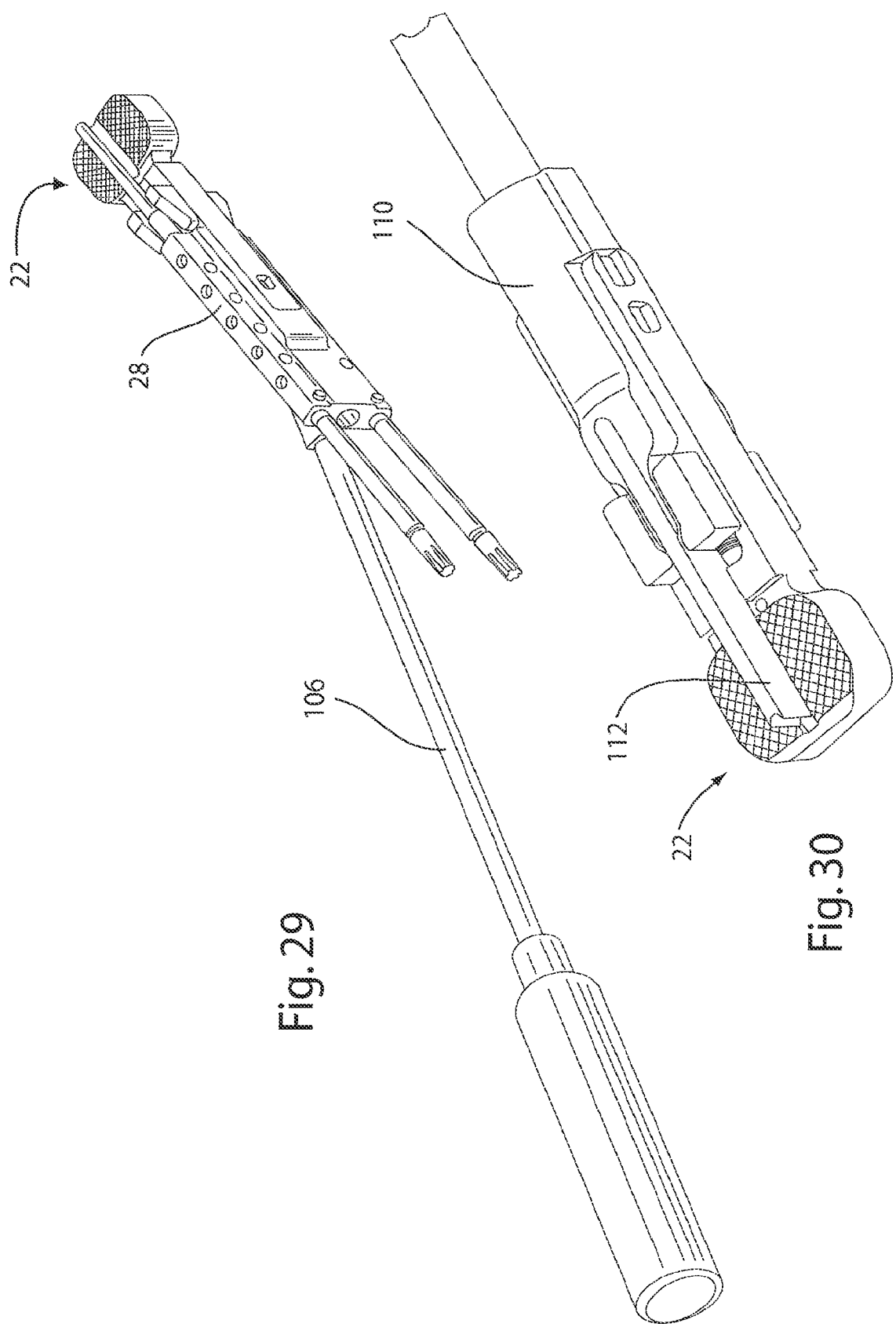

DRILLING/MILLING GUIDE AND KEEL CUT PREPARATION SYSTEM

CROSS REFERENCE TO RELATED APPLICATIONS

This application is a divisional application of U.S. application Ser. No. 12/375,710, filed Oct. 2, 2009, entitled "Drilling/Milling Guide And Keel Cut Preparation System," the entire disclosure of which is incorporated by reference in its entirety herein for all purposes. U.S. application Ser. No. 12/375,710 is a national stage application under 35 U.S.C. §371 based on International Application No. PCT/US07/74717, filed on Jul. 30, 2007, the entire disclosure of which is incorporated by reference in its entirety herein for all purposes. Each application listed above claims the benefit of U.S. Application Ser. No. 60/834,178, filed Jul. 31, 2006, the entire disclosure of which is incorporated by reference in its entirety herein for all purposes.

TECHNICAL FIELD

This invention relates to intervertebral implants, and more specifically, it relates to new and improved guides, systems and methods for cutting a keel slot in preparation for inserting an intervertebral implant in the intervertebral space.

BACKGROUND

Currently, when it is necessary to completely remove a disc from between adjacent vertebrae, the conventional procedure is to fuse the adjacent vertebrae together. More recently, there have been important developments in the field of disc replacement, namely disc arthroplasty, which involves the insertion of an artificial intervertebral disc implant into the intervertebral space between adjacent vertebrae. This then allows limited universal movement of the adjacent vertebrae with respect to each other.

Some instruments have been developed to date for preparing an intervertebral space for receiving an artificial disc implant. These include a set of different sizes of trial implants, different ones of which are inserted into a cleaned out intervertebral space until the correct size trial implant has been determined, thereby determining the size of the actual disc implant to be permanently inserted. The trial implant may have a fixed stop member in the form of a pin fixed to the rear end of the trial implant and extending vertically up and down for limiting movement of the trial implant into the intervertebral space.

Some disc implants have a raised keel on each endplate which requires that a cutout be formed in the vertebrae adjacent the intervertebral space for receiving these raised keels. One known arrangement for forming these cutouts is with a chisel which can be mounted to move along slots in the top and bottom of the selected trial implant as the chisel cuts into the adjacent vertebrae to form the cutouts.

Besides a slot made by chiseling, drilling or milling can also be used, and combinations of these procedures are possible as well. However, where a chisel cut is made using a chisel and a mallet, quite high forces are applied in direction of the cut. With drilling, lesser forces are applied, but the drill can slip of or bend during drilling. With milling, a precise cut is made without high forces, but the milling tool needs to have a certain diameter, because otherwise it will break during milling and consequently milling is not always possible where a long narrow cut is required. Thus, a procedure used to perform narrow cuts without applying high forces is desirable. Exemplary of such prior art devices and methods are those disclosed in USPA 2004-0215198 (Marnay et al.) and USPA 2006-0064100 (Bertagnoli et al.), which are hereby incorporated by reference.

One known artificial disc implant is shown in Published Application No. WO 01/01893, published Jan. 11, 2001; and instruments for inserting same are shown in U.S. Pat. No. 7,118,580 (Beyersdorff—or Published Application No. WO 01/19295) and USPA 2004-0215198 (Marnay—or Published Application No. WO 04/098380). These references are also hereby incorporated by reference.

While these known instruments and methods represent a substantial improvement in the art, there exists a continuing need for improvements in the field of instruments and methods for preparing an intervertebral space for receiving an artificial intervertebral disc implant.

SUMMARY

In accordance with an exemplary embodiment of the present invention, there is provided a milling guide for use with an instrument system for preparing an intervertebral space defined by two adjacent vertebra. The instrument system can include a trial head sized to be received in the intervertebral space, and a tool for preparing at least one of the two adjacent vertebras. The milling guide can include a milling guide body defining a proximal end and a distal end that is spaced from the proximal end along a first direction. The milling guide is configured to be supported relative to the trial head. A chamber can be coupled to the milling guide body, the chamber being elongate along the first direction. A pivot element can be pivotally coupled to the milling guide body and configured to at least partially receive the tool. The pivot element can be configured to pivot relative to the chamber about a pivot axis that extends in a second direction that is substantially transverse to the first direction, wherein the pivot element is configured to pivot about the pivot axis when 1) the milling guide is supported relative to the trial head, 2) when the trial head is received in the intervertebral space.

In accordance with another exemplary embodiment of the present invention, there is provided a milling guide that can includes a milling guide body defining a proximal end and a distal end that is spaced from the proximal end along a first direction. The milling guide is configured to be supported relative to the trial head. A first pivot element can be pivotally coupled to the milling guide body and configured to at least partially receive the tool. The pivot element can be configured to pivot about a first pivot axis that extends in a second direction that is substantially transverse to the first direction. A second pivot element can be pivotally coupled to the milling guide body and configured to at least partially receive the tool or another tool. The second pivot element can be configured to pivot relative to the first pivot element about a second pivot axis that extends in the second direction, wherein the second pivot element is configured to pivot about the second pivot axis when 1) the milling guide is supported relative to the trial head, and 2) when the trial head is received in the intervertebral space.

In accordance with another exemplary embodiment of the present invention, there is provided a milling guide that can include a milling guide body defining a proximal end and a distal end that is spaced from the proximal end along a first direction. The milling guide can be configured to be supported relative to the trial head. A first chamber pivotally can be coupled to the milling guide body and configured to at least partially receive the tool. The first chamber can be configured to pivot about a first pivot axis that extends in a second direction that is substantially transverse to the first direction. A second chamber can be pivotally coupled to the milling guide body and configured to at least partially receive the tool. The second chamber can be configured to pivot relative to the first chamber about a second pivot axis that extends in the second direction, wherein the second chamber is configured to pivot about the second pivot axis when 1) the milling guide is supported relative to the trial head, and 2) when the trial head is received in the intervertebral space.

BRIEF DESCRIPTION OF THE DRAWINGS

FIG. 1 is a perspective view of an intervertebral implant adjacent an intervertebral space between two vertebral bodies.

FIG. 2 is a perspective view of the vertebral bodies now having keel slots provided therein.

FIG. 3 is a perspective view of an intervertebral implant partially inserted into the intervertebral space between two vertebral bodies.

FIG. 4 is a perspective view of the intervertebral implant fully inserted into the intervertebral space between two vertebral bodies.

FIG. 5 is a front, side and plan perspective view of a milling system in accordance with the present invention.

FIG. 6 is a back, side and plan perspective view of the milling system of FIG. 5 positioned with the trial implant in an intervertebral space.

FIG. 7 is a front, side and plan perspective view of a trial implant in accordance with the present invention.

FIG. 8 is a front, side and plan perspective view of the trial implant of FIG. 7 with an attached handle.

FIG. 9 is a front, side and plan perspective view of a milling guide in accordance with the present invention.

FIG. 10 is a cross sectional front, side and plan perspective view of the milling system of FIG. 5.

FIG. 15 is a back, side and plan perspective view showing the initial insertion of a reamer into the milling guide of FIG. 9 mounted on the trial implant of FIG. 12.

FIG. 16 is a back, side and plan perspective view showing the initial cutting using the reamer in the milling guide mounted on the trial implant.

FIG. 21 is an enlarged partially cross sectional front, side and plan perspective view showing the keel cut made with the reamer using the cutting action depicted in FIGS. 18-20.

FIG. 22 is a back, side and plan perspective view of an alternative design where the proximal end of the milling guide has bearings.

FIG. 23 is a plan view of an alternative design of a trial implant head with a through hole.

FIG. 29 is a back, side and plan perspective view of a handle attached to the milling system of FIG. 5.

FIG. 30 is a front, side and plan perspective view of an alternate milling guide used with a box chisel.

DETAILED DESCRIPTION OF ILLUSTRATIVE EMBODIMENTS

Figure 12:
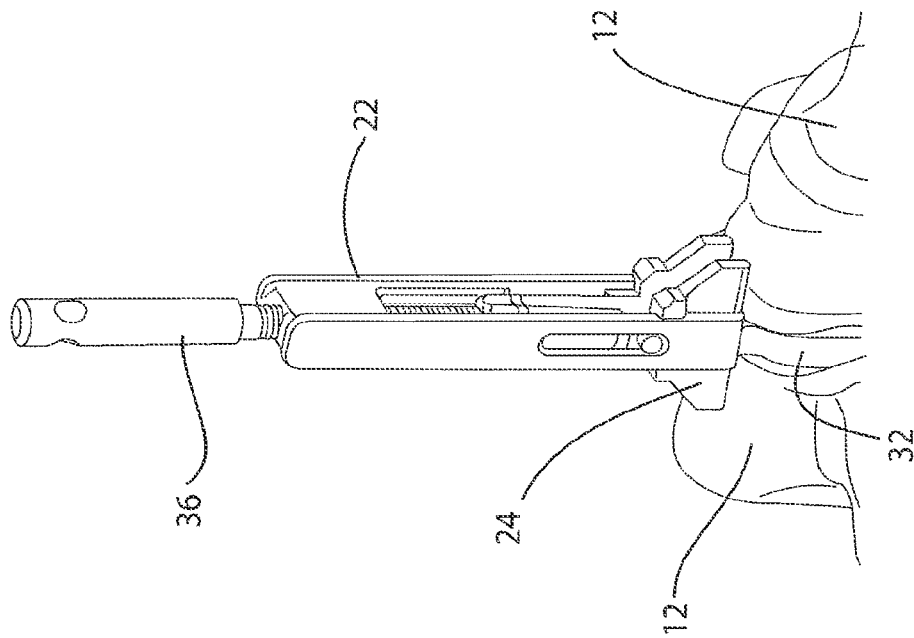
FIG. 12 is a back, side and plan perspective view of the trial implant of FIG. 11 positively positioned in the intervertebral space.
Figure 11:
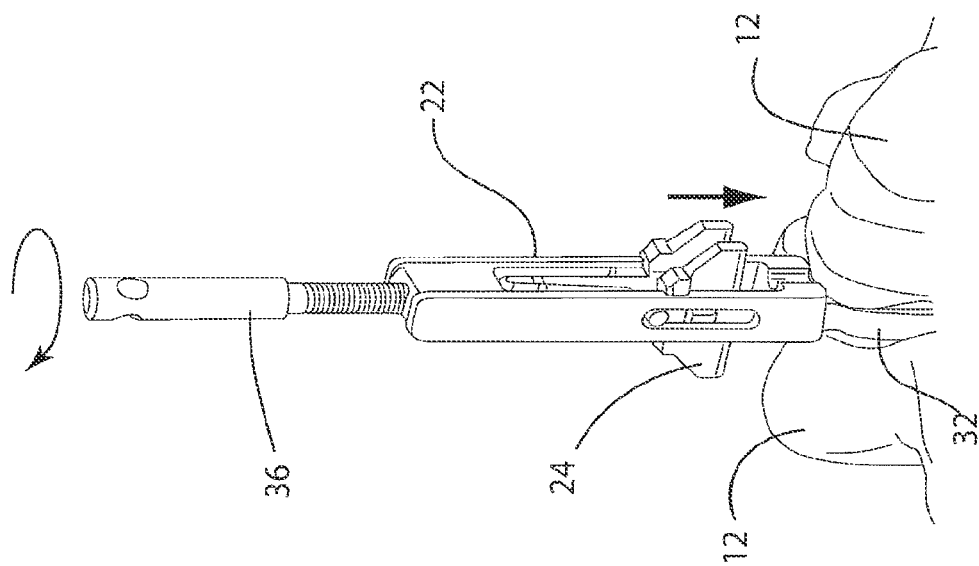
FIG. 11 is a back, side and plan perspective view of the trial implant of FIG. 7 inserted in the intervertebral space as an adjustable stop is adjusted.

At present, the intervertebral implant is normally inserted from the patient's anterior moving towards the patient's posterior. However, it is to be understood that the implant, the instruments and the method can also be designed and arranged to insert the implant laterally, i.e., from the side, in which case the keels will be oriented on the implant for such lateral movement and the cutouts in the adjacent vertebrae will be opened toward a lateral side to receive the keel. To avoid confusion with respect to the patient's anatomy, the invention will be described herein with respect to more simple terminology which relates to the instruments and methods themselves. For example, in describing the invention, the terms "front", "forward" or "distal" mean the part of the instrument which faces toward the vertebrae or is moving in the direction of movement toward the vertebrae, while the words "back", "rear", "rearward", or "proximal" refer to the end of the instrument farthest from the vertebrae or moving away from the vertebrae. Also, in this application, the words "upper" or "lower" or "uppermost" or "lowermost" or any other words describing the orientation of the intervertebral implant or the instruments or methods associated therewith are used only for convenience and are not intended to convey any limitation. More specifically, the parts of the implant, the instruments and/or the methods described in this application with reference to the upper part can in fact be positioned as the superior or inferior part within the patient's vertebrae, with the other of the two parts being the opposite part.

The instruments and methods described herein are applicable for preparing a wide range of artificial disc implants for insertion into an intervertebral space, typically for TDR (total disc replacement). For those instruments and methods described herein which include the concept of forming cutouts to receive raised keels, the instruments and methods described herein are adaptable for use with any artificial disc implant having such keels. Thus, the depiction and description of the referenced implant is exemplary.

With reference now to the drawings in which like numerals represent like elements throughout the various views, it will initially be appreciated that the present invention is directed to improving the primary stability of an intervertebral implant 10, such as that disclosed U.S. Pat. No. 7,204,852 (Marnay et al.), which is located between adjacent vertebral bodies 12 (for fusion or non-fusion procedures) as shown in FIGS. 1-4. Implant 10 is designed with a keel 14 on both endplates 16 contacting the adjacent vertebral bodies 12 as shown in FIG. 1. In order to position implant 10 into the disc space provided after a discectomy, a cut needs to be made in the inferior as well as in the superior vertebral bodies 12 to provide slots 18 as shown best in FIG. 2. Implant 10 is shown partially between vertebral bodies 12 in FIG. 3, and then fully inserted in FIG. 4.

The large majority of surgical techniques for TDR use chisels to perform or prepare the keel cuts or slots 18. However, in accordance with the present invention, a drilling/milling system 20 has been developed as an alternative in cases with hard bone and/or sclerotic endplates in order to reduce the impact forces and in order to improve the cleaning of the posterior aspect of the keel cut. Milling system 20 includes the following instruments that interact with each other as broadly shown in FIGS. 5-6: a trial implant 22 with an adjustable stop 24; a detachable handle 26 for trial implant 22 (shown only in FIG. 8); a milling guide 28; and a reamer 30 (which is used with existing/known power tool equipment).

Trial implant 22 is shown in greater detail in FIG. 7. It fulfills the known function of determining a correct height of implant 10 to be used, for example where implant 10 comes in different heights, there will be a different trial implant 22 to accommodate each height (such as 5 mm, 6 mm and 7 mm). A selected trial implant 22 having a one-piece implant head 32 is thus inserted between the vertebral bodies 12 with the help of detachable handle 26 to see if the selected trial head 32 fits properly, so that the correct implant height (and size, if desired) is then known. Obviously, various heights of trial implants 22 with corresponding heads 32 are available for such a trial and error determination; and if desired, different sized footprint and/or shapes of implants, etc. can also be tried if desired to determine the best implant 10 to be used. In accordance with the present invention, once the correct size of trial implant 22 is inserted, the body 34 of trail implant 22 then subsequently serves as a base for milling guide 28 to be connected to or to be mounted on.

As shown in FIG. 8, the detachable handle 26 is removably attached (as by a ball/detent interaction) to the threaded shaft 36 of adjustable stop 24 for convenience. It will be appreciated that the adjustable stop 24 (shown in FIG. 7) as well and is movably mounted in the rear of body 34 of trial implant 22 by threaded shaft 36. Adjustable stop 24 includes upper and lower vertebra engaging members 38 whose longitudinal position relative to trial head 32 is thus adjustable. Engaging members 38 are attached to shaft 36 and guided for movement in trial body 34 as shown, and engaging members 38 are positioned symmetrically relative to the midline of trial implant 22 for an improved resistance to A/P forces. In addition, the split design of engaging members 38 allows reamer 30 to move in between the two engaging members 38, with engaging members 38 offering additional soft tissue protection from reamer 30. Alternatively, trial implant 22 could include only one side stop member or two stop members placed on either side of the upper and lower vertebral bodies 12. Trial implant 22 includes a central groove 40 in trial head 32 on the cranial (upper) side and on the caudal (lower) side into which reamer 30 can be moved or plunged into. Alternatively, trial body 32 could include a cavity through the entire (split/forked) trial with the same function.

Milling guide 28 is best shown in FIG. 9. Milling guide 28 is designed to connect to a trial body 34 of the trial implant 22. This connection occurs as milling guide 28 is guided for movement along shaft 36 at the rear of trial implant 22 and additionally guided by guidance feature 42 running along most of the length of trial implant 22 as best seen in FIG. 7. This guidance feature 42 is a combination of short flanges 44 outstanding along either side (upper and lower) of trial body 34 and correspondingly spaced and shaped grooves 46 provided in the mating surfaces of milling guide 28. Milling guide 28 is positioned on trial body 34 until stop surfaces 48 mate up with the rear end of trial body 34 which results in a fixed distance between the proximal end of milling guide 28 and the distal end of trial implant 22. Preferably, a locking mechanism 50 is used to prevent the milling guide 28 from unintentionally disengaging from the trial implant 22 and/or to eliminate any clearance/play between the milling guide 28 and the trial implant 22. Locking mechanism 50 is shown as mating wedges 52, but leaf springs, locking screws, or other mechanisms known in the art could be used. Milling guide 28 also includes a handle attachment member 53 on one side to which a handle (such as handle 106 in FIG. 29) is removably attached by a threaded connection.

Figures 17, 18:
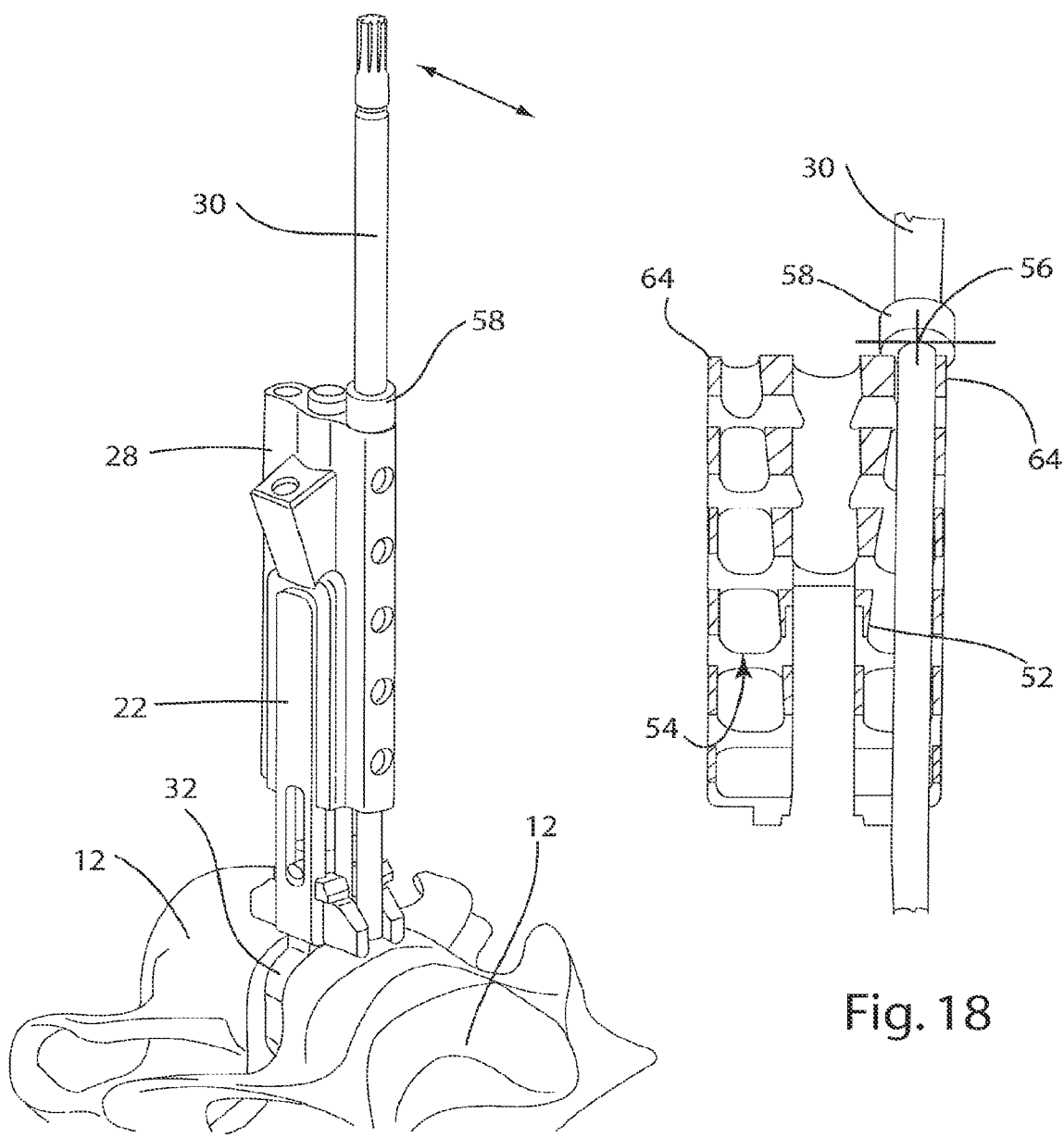
FIG. 17 is a back, side and plan perspective view showing the complete cutting using the reamer where a stop thereon engages the milling guide mounted on the trial implant.
FIGS. 18-20 are cross sectional front, side and plan perspective views showing the cutting action of the reamer in the milling guide.
Figure 19:
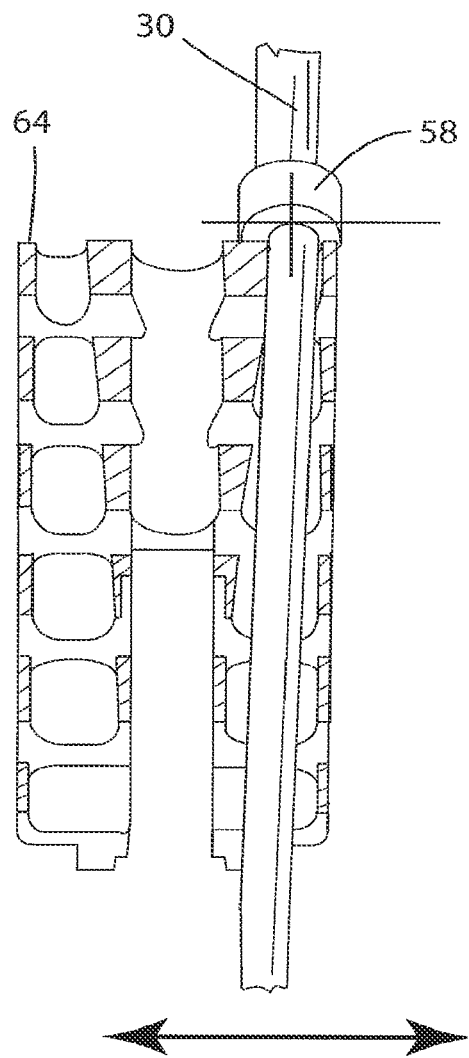
Figure 20:
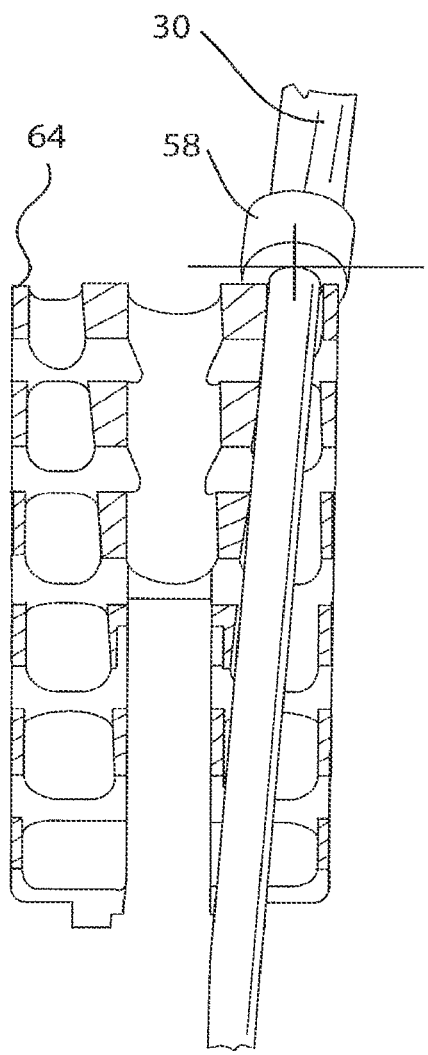

As shown in FIG. 10, the milling guide 28 defines upper and lower chambers 54 which guide respective reamers 30. Each chamber 54 is tapered from the front to the rear as shown in FIGS. 18-20 to allow for a windshield wiper milling cycle 60 (see arrow in FIG. 19, and compare the reamer 30 position in FIGS. 18-20) around a pivot axis 56 located at the rear end of the milling guide. In the embodiment shown, the reamer 30 is restricted laterally, and is allowed milling in only a cranial-caudal direction. However, in alternate embodiments, chambers 54 could allow for milling in at least one other direction up to all directions. The milling function and technique is described in more detail hereafter. Further, chamber 54 could also be more cylindrical in nature to allow for a more translational milling cycle in cranial-caudal direction.

As an alternative to the disclosed embodiment, it will be appreciated that milling guide 28 could instead include only one reamer guiding chamber 54 which would be positioned on one (upper or lower) side of trial implant 22. Then, after completing the first keel cut, reamer 30 would then be retracted, the milling guide turned by 180 degree and reinserted before milling the second (other side) keel cut. The reamer could also be pre-assembled to such a milling guide, to easily allow this milling guide to retract a certain distance before turning and reinsertion for the other keel cut. As another alternative, the milling guide and the trial implant could be designed as one instrument with the same functions described above.

As desired, different reamers 30 could be used with system 20 depending on whether drilling and/or milling (side cutting) capabilities are primarily needed. Exemplary reamers would thus include, for example, regular drills, Lindemann reamers, cranial burrs, and other reamers as known and used in the art can also be used as desired. The cutting end of reamer 30 is preferably conically shaped, with a smaller diameter at the distal (forward) end slowly expanding towards the bigger shaft diameter. The benefit of the conical shape is that the smaller tip compensates for the small play of the reamer within chamber 54 of the milling guide 28. But alternatively, the reamer tip might be cylindrical, tapered or a combination of cylindrical, tapered and/or conical as desired. Each reamer 30 also includes an integrated bushing 58 which will come to rest against the back end of milling guide 30 to control the depth of penetration of reamer 28 into vertebral body 12, in conjunction with the use of adjustable stop 24 as noted above. When bushing 58 comes to rest against the back end, it acts as a bearing member against the back end as described more fully below.

Figure 14:
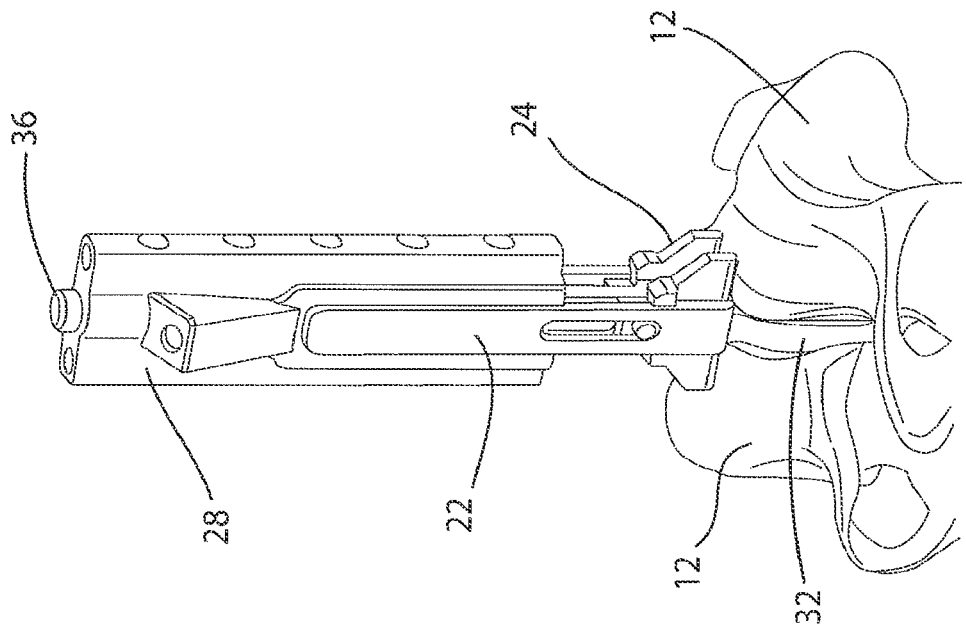
FIG. 14 is a back, side and plan perspective view of the trial implant of FIG. 12 with the milling guide of FIG. 9 mounted thereon.
Figure 13:
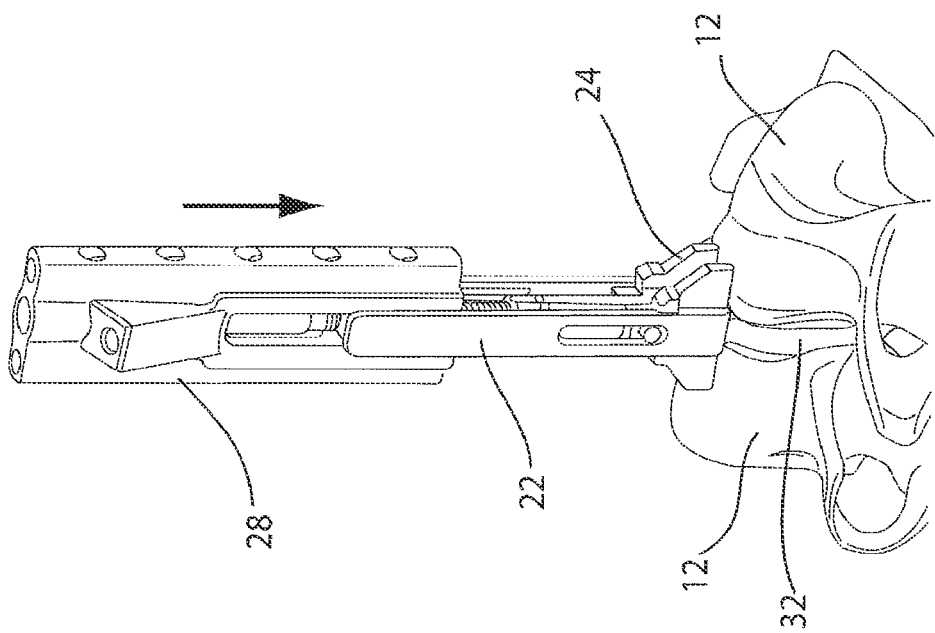
FIG. 13 is a back, side and plan perspective view of the trial implant of FIG. 12 as the milling guide of FIG. 9 is mounted thereon.

In use, the drilling/milling system 20 is used in the following manner and with reference to FIGS. 11-17. Initially, after performing the discectomy (FIG. 1), the surgeon uses the trial implants to find the correct height (and footprint size if desired) of the implant 10 that will be needed for each particular vertebral space. As each, and more importantly, as the final or correct, trial implant is inserted with the integrated adjustable stop 24 (FIG. 11), the adjustable stop 24 not only secures the trial implant 22 in its right position relative to the vertebral bodies 12 but it also assures that the trial implant 22 will not slide further back into the spinal canal (FIG. 12). Once the right size and correct position has been found, the milling guide 28 is mounted to the trial body 34 by sliding the milling guide 28 over the trial body 34 using a guidance feature 42 (FIG. 13) and locking the milling guide 28 to trial body 34 with locking mechanism 50 (FIG. 14).

Next, the surgeon performs the first cut on the vertebral body 12 of his choice. Using a reamer or drill with side cutting capabilities, the surgeon first drills/cuts straight into vertebral body 12 until bushing 58 on reamer 30 is stopped by the milling guide 28 as shown by FIGS. 15-17. Then, the surgeon sweeps in the direction of the endplate to complete the keel cut as shown in FIGS. 18-20. The surgeon could also start the cut by drilling/cutting along the endplate and then sweeping into the vertebral body if desired, or by drilling intermediate the two and sweeping both up and down. Bushing 58 when placed on the reamer 30 avoids drilling/cutting too deep into vertebral body 12, while acting as a bearing member against the back end of milling guide 30. Depicted in FIG. 21 is an enlarged view of a keel cut or slot 18 made with system 20.

Figure 31:
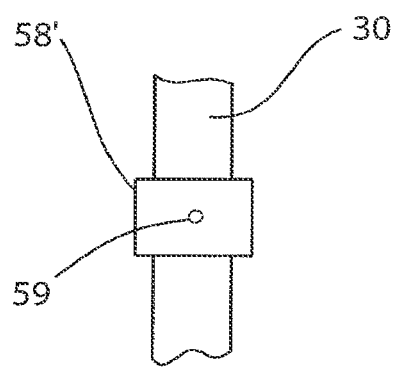
FIG. 31 is side elevation view of an adjustable bushing mounted on a portion of a reamer.

Finally, the surgeon removes reamer 30 and repeats the same operation on the other vertebral body 12. FIG. 2 shows both keel cuts 18 as made by system 20 in the respective vertebral bodies 12. The cutting tool is conveniently powered by any known power tool, such as E-pen, MidasRex, Stryker TPS, etc. The first used reamer 30 could also be left in place after completing the cut or the first drilling hole to stabilize the construct while using a second reamer to mill the keel cut on the opposite side, as shown in FIG. 10 depicted both reamers 30. If the bone is extremely hard, reamer 30 could also be used as a drill several times to weaken the bone before completing the keel cut with the sweeping milling step. Bushing 58 acting as a stop on reamer 30 could alternatively be detachable, or adjustable to allow for different drilling/milling depths, as shown by bushing 58' in FIG. 31. Bushing 58' is adjustable by disengagement of a simple set screw 59 or the like.

It will be noted that milling guide 28 provides tapered mill chambers 54 which allow the reamer to pivot about the proximal end of the guide as shown in FIG. 18-20. For this reason, the proximal (rearward) end 64 of milling guide 28 is slightly curved towards the cranial and caudal ends. This allows reamer 30 to drop slightly deeper when angling towards trial body 32, resulting in a straighter wall at the posterior end of keel cut 18 instead of an arc as would be expected from such a pivoting motion. Alternatively, the proximal end of milling guide 28 could also be straight if such an arced end is not objectionable. It will also be appreciated that the slimness and shape of system 20 also allows good visibility for the surgeon.

Depicted in FIG. 22 is an alternate design of a proximal end 66 of milling guide 28 in which a pivot element 68 with a sleeve bearing 70 therein is provided in proximal end 66 for each mill chamber 54. Sleeve bearing 70 receives the shaft of reamer 30 in order to minimize friction between the milling guide 28 and reamer 30. Sleeve bearing 70 is conveniently supported by pivot elements 72 rotating around small pins (not shown) which allow a controlled sweeping motion of reamer 30.

Depicted in FIG. 23 is an alternative embodiment of a trial implant head 76 with a through hole 78 therein. Through hole 78 allows the necessary room for reamers 30, and strength of trial head 76 is not compromised since the forward part of trial head 76 is closed as shown. Through hole 78 is provided to improve the retention in trial head 76 of the cut bone material created during the reaming process.

Figure 24:
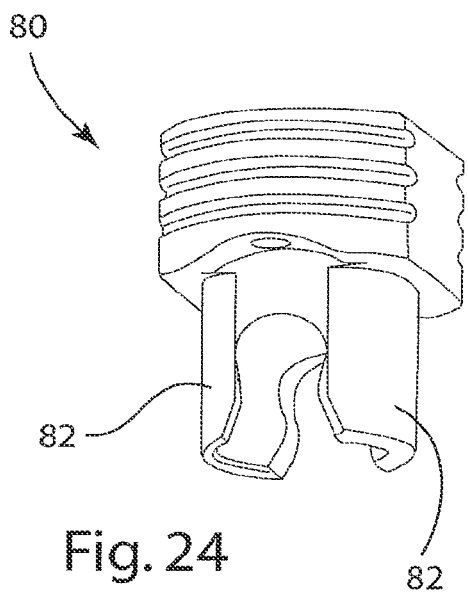
FIG. 24 is back, side and plan perspective view of an alternative design of a disposable pivot element.
Figure 25:
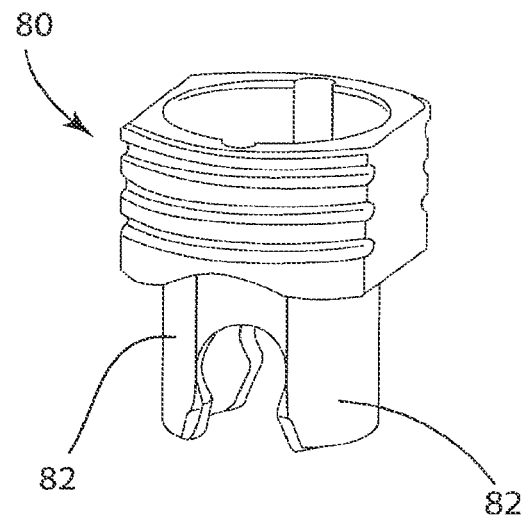
FIG. 25 is a front, side and plan perspective view of the disposable pivot element depicted in FIG. 24.

Depicted in FIGS. 24-25 is an alternative disposable pivot element 80 similar to pivot element 68 described above. If the life span of the sleeve bearing therein (not shown) is considered too short or reuse is not desired, then pivot element 80 supporting the sleeve bearing is made disposable. The sleeve bearing and pivot element 80 would then be replaced in the milling guide after each surgery. The material used for this type of pivot element could be PEEK. A pair snap-on spring-like receiving feet 82 provided on pivoting element 80 allows pivot element 80 to be attached to and detached from pins 84 (see FIG. 22) at the rear end of the milling guide.

Figure 33:
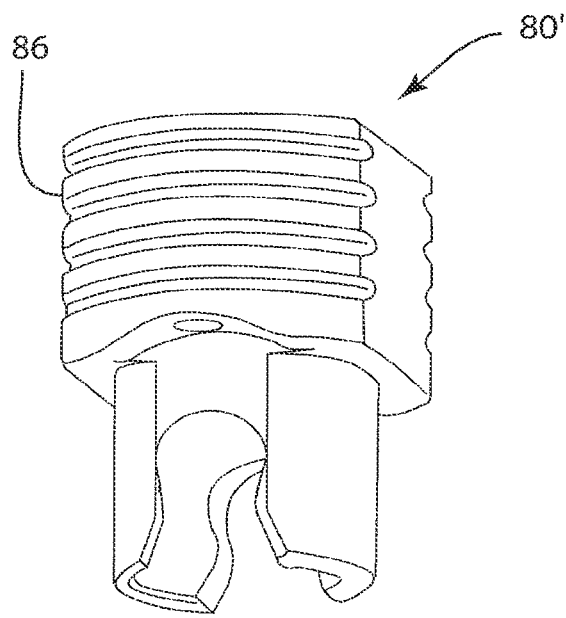
FIG. 33 is a back, side and plan perspective view of an alternative, taller pivot element to that shown in FIG. 25.

Alternatively, pivot element 80 could be made in different heights, such as shown by pivot element 80' in FIG. 33 which is taller than pivot element 80 due to the height of head 86 (though alternatively, the portion below head 86 could instead be heightened). With different heights of pivot elements, the surgeon would select the height desired to position the cutting end of reamer 30 relative to where bushing 58 contacts the pivot element as needed. Such pivot elements 80' may or may not be designed to be disposable.

Figure 26:
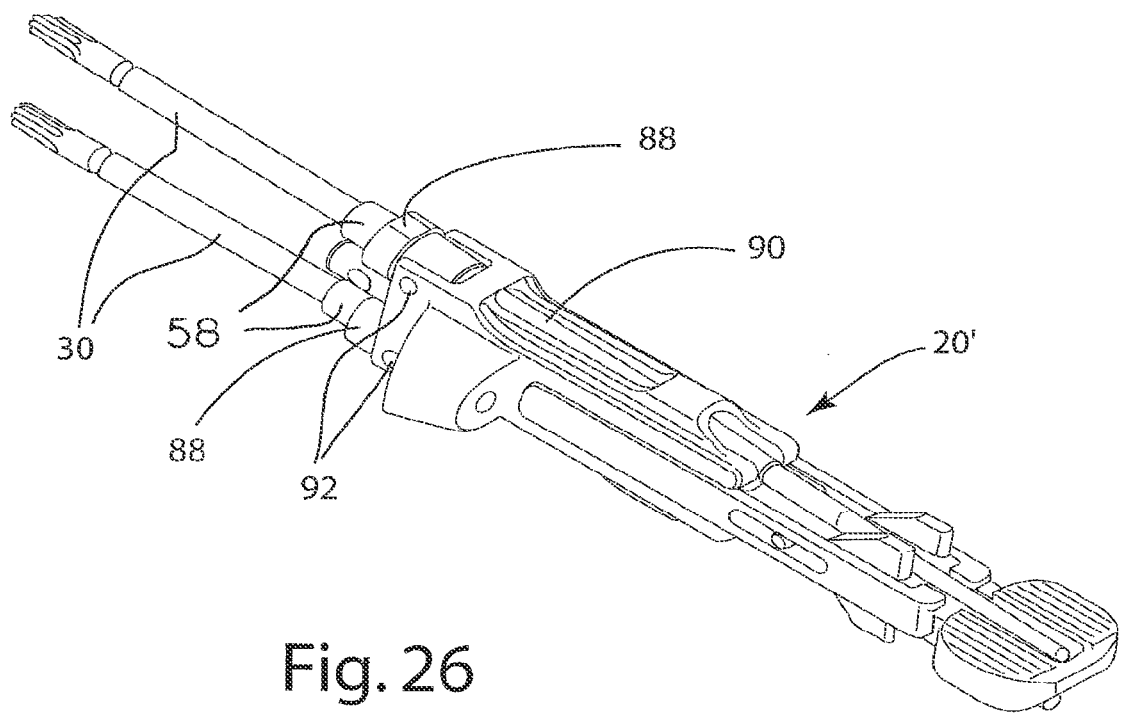
FIG. 26 is a back, side and plan perspective view of another alternative milling system with a pivot element having an elongated tube.
Figure 32:
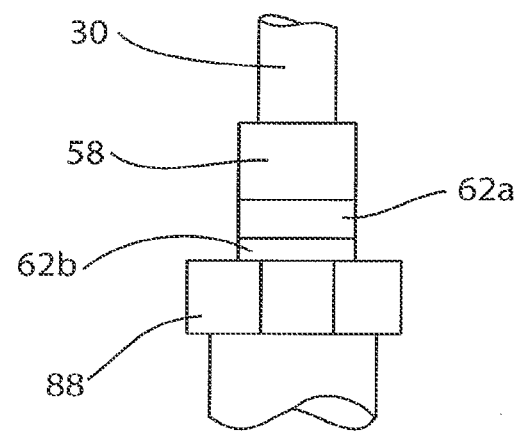
FIG. 32 is side elevation view of a bushing mounted on a portion of a reamer together with spacing washers.

Depicted in FIG. 26 is another alternative embodiment of a milling system 20' having a pivot element 88 including an elongated tube 90 designed to provide guidance for reamer 30. Elongated tube 90 extends from the bearing/pivot portion at mounting pins 92 to the distal (forward) end of the milling guide to provide enhanced support for reamer 30 if needed or desired. As another alternative, one or more thin spacing washers 62a and/or 62b as depicted in FIG. 32 could be added as needed below bushing 58. Washers 62 are used to space bushing 58 slightly further from pivot element 88 (or from milling guide 28 in other embodiments noted above), and thus would become part of the bearing member for reamer 30 against the back end of milling guide 28. Washers 62a and 62b have different heights as shown, and one or more of each, or others of different heights, could be used as desired. Such washers would preferably slide frictionally along reamer 30 so that washers 62 would not move along reamer 30 without being positively moved, and hence would not fall off of reamer 30 accidentally.

Figure 27:
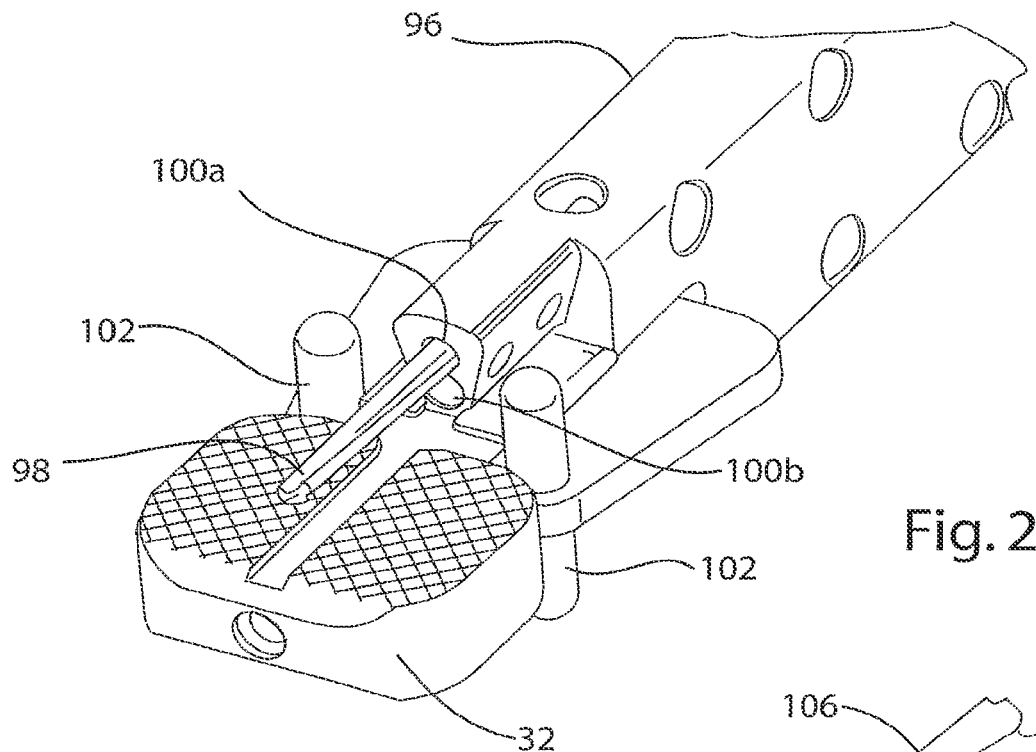
FIG. 27 is a front, side and plan perspective view of an alternative milling guide used for drilling.
Figure 28:
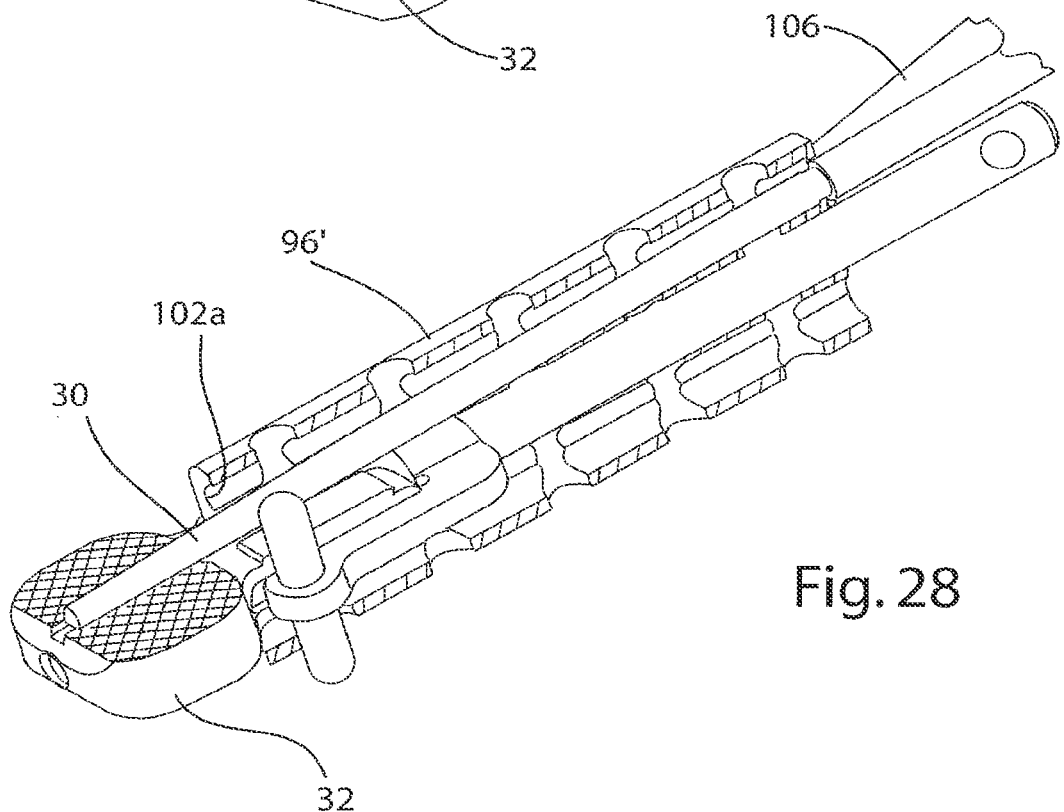
FIG. 28 is a front, side and plan perspective view of a modified embodiment of the alternative milling guide depicted in FIG. 27.

Depicted in FIG. 27 is an alternative embodiment of a milling guide 96 for straight hole drilling or cutting. Milling guide 96 is provided as an option when it is desired to reduce the impact forces for a subsequent chiseling step used to form the keel cut as typical in the prior art. The keel cutting technique would include drilling of one or two parallel straight holes per keel using a drill 98 to remove bone before using either a wedged and/or box chisel (not shown). For this purpose, milling guide 96 includes two guide holes 100a and 100b for each keel cut location. The system shown also has an alternative adjustable stop design having two side stops 102 positioned symmetrically relative to the insertion or longitudinal axis. In order to remove more bone of the vertebral endplates, hole 102b in milling guide 96 could be angled towards the trial body as shown in FIG. 28 with milling guide

96'. If reamer 30 has a tapered/conical tip, the resulting drilled hole caused by the tapered/conical tip would be designed to be parallel to the trial surface, or at least allow for more bone removal at the proximal (forward) end of the trial body. In the figure, the surgeon would drill two holes on each side, but the two holes on each side would not be parallel.

If desired, any of the milling (or drilling) guides is stabilized or controlled with a guide handle 106 as shown in FIG. 29 (and also partially in FIG. 22). Alternatively, guide handle 106 could also be attached to a retainer or a retractor system such as the SYNFRAME® by Synthes.

If the surgeon feels comfortable with chiseling to perform the keel cut, trial implant 22 can also accommodate a guide 110 for a box chisel 112 as shown in FIG. 30. Guide 110 is mounted similarly to milling guide 28, allowing the surgeon to use either a drill or a chisel method to perform the keel cut as desired.

Figure 34:
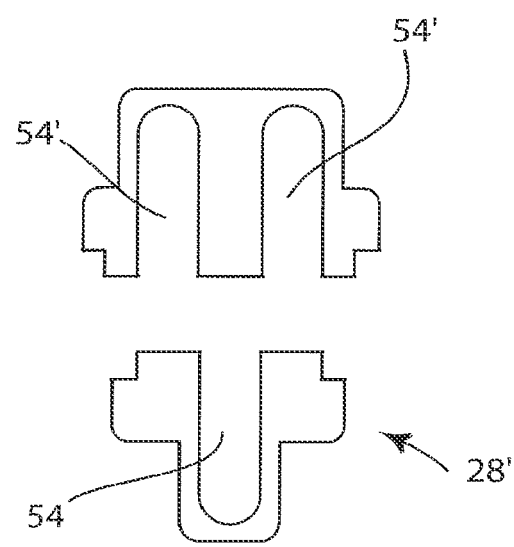
FIG. 34 is a front elevation view of an alternative milling guide to that shown in FIG. 9 having two mill chambers on the upper part.

While the above embodiments have been depicted where an upper and lower keel slot is made in the adjacent vertebral bodies 12, there may be situations where an implant has side by side or dual (or more) keels on one (or both) sides, so that cutting of two keel slots is desired in a vertebral body 12. In such situations, it would be possible to provide a milling guide 28' as shown in FIG. 34. Milling guide 28' has two side by side mill chambers 54' on the top portion, with a corresponding rear end (not shown) for accommodating a reamer 30 in each mill chamber 54'. A trial implant (not shown) which accommodates the two mill chambers with twin trial grooves would thus also be provided.

While the components described above are preferably made out of metals such as stainless steel, titanium or titanium alloy, alternatively some components could be made out of composites or polymers. In addition, this type of bone cut procedure is not limited to the cervical spine, but could be used any where in the human body and in particular it could be applied for Lumbar TDR.

Although the invention has been described in considerable detail with respect to preferred embodiments thereof, it will be apparent that the invention is capable of numerous modifications and variations, apparent to those skilled in the art.

What is claimed:

1. A milling guide for use with an instrument system for preparing an intervertebral space defined by two adjacent vertebrae, the instrument system including a trial head sized to be received in the intervertebral space, the milling guide comprising:
   a milling guide body defining a proximal end and a distal end that is spaced from the proximal end along a first direction, the milling guide configured to be supported relative to the trial head;
   a chamber coupled to the milling guide body, the chamber being elongate along the first direction; and
   a pivot element coupled to the milling guide body and defining a channel that extends through the pivot element such that the channel is configured to at least partially receive a tool for preparing at least one of the two adjacent vertebrae, the pivot element configured to pivot relative to the milling guide body about a pivot axis that extends through both the milling guide body and the channel in a second direction that is substantially transverse to the first direction,
   wherein the pivot element is configured to pivot about the pivot axis when 1) the milling guide is supported relative to the trial head, and 2) when the trial head is received in the intervertebral space.

2. The milling guide as in claim 1, further comprising a pin that extends from the milling guide body to the pivot element in the second direction so as to pivotally couple the pivot element to the milling guide body.

3. The milling guide as in claim 2, wherein the pivot element comprises an elongate member, wherein the elongate member is coupled to the pin.

4. The milling guide as in claim 1, wherein the proximal end of the milling guide body comprises a bearing mechanism coupling the milling guide body to the pivot element, where the bearing mechanism defines the pivot axis when the tool is at least partially received in the pivot element.

5. The milling guide as in claim 4, wherein the bearing mechanism is a movable bearing mounted in the proximal end of the milling guide body.

6. The milling guide as in claim 1, wherein the chamber defines an inner shape that is at least partially tapered.

7. The milling guide as in claim 1, wherein the chamber defines an inner shape that is generally cylindrical.

8. The milling guide as in claim 1, wherein the milling guide body defines a first end and a second end that is spaced from the first end along a third direction that is substantially perpendicular to the first direction and the second direction, wherein the pivot element is disposed on either the first end or second end of the milling guide body, and wherein the chamber is disposed on the other of the first end or the second end of the milling guide body.

9. The milling guide of claim 1, further comprising:
   a second pivot element pivotally coupled to the milling guide body and configured to at least partially receive the tool or another tool, the second pivot element configured to pivot relative to the first pivot element about a second pivot axis that extends in the second direction,
   wherein the second pivot element is configured to pivot about the second pivot axis when 1) the milling guide is supported relative to the trial head, and 2) when the trial head is received in the intervertebral space.

10. The milling guide as in claim 9, further comprising a pin pivotally coupling the pivot element to the milling guide body.

11. The milling guide as in claim 10, further comprising a second pin pivotally coupling the second pivot element to the milling guide body.

12. The milling guide as in claim 10, wherein the pivot element comprises an elongate member, wherein the elongate member is coupled to the pin.

13. The milling guide as in claim 11, wherein the second pivot element comprises a second elongate member, wherein the second elongate member is coupled to the second pin.

14. The milling guide as in claim 9, further comprising a second chamber coupled to the milling guide body, the second chamber being elongate along the first direction.

15. The milling guide as in claim 14, wherein the second chamber defines an inner shape that is at least partially tapered.

16. The milling guide as in claim 14, wherein the second chamber defines an inner shape that is generally cylindrical.

17. The milling guide as in claim 9, wherein the milling guide defines a first end and a second end that is spaced from the first end along a third direction that is substantially perpendicular to the first direction and the second direction, wherein the first pivot element is disposed on either the first end or second end of the milling guide body, and wherein the second pivot element is disposed on the other of the first end or the second end of the milling guide body.

18. The milling guide as in claim 9, wherein the proximal end of the milling guide body comprises a bearing mechanism coupling the milling guide body to the pivot element, where the bearing mechanism defines the pivot axis when the tool is at least partially received in the pivot element.

19. A milling guide for use with an instrument system for preparing an intervertebral space defined by two adjacent vertebrae, the instrument system including a trial head sized to be received in the intervertebral space, the milling guide comprising:
- a milling guide body defining a proximal end and a distal end that is spaced from the proximal end along a first direction, the milling guide configured to be supported relative to the trial head;
- a chamber coupled to the milling guide body, the chamber being elongate along the first direction; and
- a pivot element coupled to the milling guide body and configured to at least partially receive a tool for preparing at least one of the two adjacent vertebrae, the pivot element configured to pivot relative to the chamber about a pivot axis that extends in a second direction that is substantially transverse to the first direction,
- wherein the milling guide body defines a first end and a second end that is spaced from the first end along a third direction that is substantially perpendicular to the first direction and the second direction, the pivot element is disposed on either the first end or second end of the milling guide body, and the chamber is disposed on the other of the first end or the second end of the milling guide body, and wherein the pivot element is configured to pivot about the pivot axis when 1) the milling guide is supported relative to the trial head, and 2) the trial head is received in the intervertebral space.

20. The milling guide as in claim 19, further comprising a pin pivotally coupling the pivot element to the milling guide body.

21. The milling guide as in claim 20, wherein the pivot element comprises an elongate member, wherein the elongate member is coupled to the pin.

22. The milling guide as in claim 19, wherein the proximal end of the milling guide body comprises a bearing mechanism coupling the milling guide body to the pivot element, where the bearing mechanism defines the pivot axis when the tool is at least partially received in the pivot element.

23. The milling guide as in claim 22, wherein the bearing mechanism is a movable bearing mounted in the proximal end of the milling guide body.

24. The milling guide as in claim 19, wherein the chamber defines an inner shape that is at least partially tapered.

25. The milling guide as in claim 19, wherein the chamber defines an inner shape that is generally cylindrical.

26. The milling guide of claim 19, further comprising:
- a second pivot element pivotally coupled to the milling guide body and configured to at least partially receive the tool or another tool, the second pivot element configured to pivot relative to the first pivot element about a second pivot axis that extends in the second direction,
- wherein the second pivot element is configured to pivot about the second pivot axis when 1) the milling guide is supported relative to the trial head, and 2) when the trial head is received in the intervertebral space.

* * * * *